US009833360B2

(12) United States Patent
Andreas et al.

(10) Patent No.: US 9,833,360 B2
(45) Date of Patent: Dec. 5, 2017

(54) TYMPANOSTOMY TUBE DELIVERY DEVICE WITH REPLACEABLE SHAFT PORTION

(71) Applicant: Tusker Medical, Inc., Menlo Park, CA (US)

(72) Inventors: Bernard H. Andreas, Redwood City, CA (US); Thomas D. Gross, Los Gatos, CA (US)

(73) Assignee: Tusker Medical, Inc., Menlo Park, CA (US)

( * ) Notice: Subject to any disclaimer, the term of this patent is extended or adjusted under 35 U.S.C. 154(b) by 192 days.

(21) Appl. No.: 14/457,293

(22) Filed: Aug. 12, 2014

(65) Prior Publication Data
US 2016/0045370 A1 Feb. 18, 2016

(51) Int. Cl.
*A61F 11/00* (2006.01)
*A61B 17/34* (2006.01)
*A61B 17/00* (2006.01)

(52) U.S. Cl.
CPC ........ *A61F 11/002* (2013.01); *A61B 17/3468* (2013.01); *A61B 2017/00398* (2013.01);
(Continued)

(58) Field of Classification Search
CPC ............ A61B 17/3468; A61B 17/3415; A61B 17/3417; A61B 17/8819; A61B 17/32002;
(Continued)

(56) References Cited

U.S. PATENT DOCUMENTS

| 858,673 A | 7/1907 | Roswell |
| 1,920,006 A | 7/1933 | Dozier et al. |

(Continued)

FOREIGN PATENT DOCUMENTS

| CN | 86105171 A | 3/1987 |
| DE | 19618585 | 11/1997 |

(Continued)

OTHER PUBLICATIONS

International Search Report and Written Opinion for International Application No. PCT/US2015/044610, dated Nov. 5, 2015.
(Continued)

*Primary Examiner* — Jocelin Tanner

(57) ABSTRACT

A tympanostomy tube delivery device comprises a shaft assembly, a pressure equalization tube, and a handpiece. All or a portion of the shaft assembly is selectively coupleable and removable from the handpiece. The shaft assembly comprises a cannula, a piercer/dilator tube, a shield tube, and a pusher tube operable to translate relative to the cannula. The pressure equalization tube is positioned within the shield tube of the shaft assembly. The piercer/dilator tube and the shield tube are operable to pierce the tympanic membrane and dilate an opening formed therein. The pusher tube is operable to drive the pressure equalization tube out of the shield tube of the shaft assembly and into the opening formed in the tympanic membrane. Upon completion of the procedure, all or a portion of the shaft assembly may then be removed and replaced.

20 Claims, 35 Drawing Sheets

(52) U.S. Cl.
CPC ............... *A61B 2017/00438* (2013.01); *A61B 2017/00787* (2013.01)

(58) Field of Classification Search
CPC ............ A61B 17/320016; A61B 17/34; A61B 17/3421; A61B 17/3209; A61B 2017/00398; A61B 2017/00438; A61B 2017/3447; A61B 2017/3443; A61B 2017/3445; A61B 2017/3449; A61B 2017/00477; A61B 2017/00787; A61B 2017/00367; A61B 2017/00389; A61B 2017/00305; A61B 2017/00309; A61B 2017/00331; A61B 2017/00353; A61B 2017/320032; A61B 2017/3433; A61B 2017/347; A61B 2010/0208; A61B 5/10511; A61F 11/002; A61F 11/004; A61F 11/006; A61F 11/00

See application file for complete search history.

(56) References Cited

U.S. PATENT DOCUMENTS

| | | | |
|---|---|---|---|
| 2,162,681 A | 6/1939 | Ryan |
| 3,473,170 A | 10/1969 | Haase et al. |
| 3,638,643 A | 2/1972 | Hotchkiss |
| 3,741,197 A | 6/1973 | Sanz et al. |
| 3,807,404 A | 4/1974 | Weissman et al. |
| 3,888,258 A | 6/1975 | Akiyama |
| 3,897,786 A | 8/1975 | Garnett et al. |
| 3,913,584 A | 10/1975 | Walchle et al. |
| 3,948,271 A | 4/1976 | Akiyama |
| 3,991,755 A | 11/1976 | Vernon et al. |
| 4,168,697 A | 9/1979 | Cantekin |
| 4,335,713 A | 6/1982 | Komiya |
| 4,335,715 A | 6/1982 | Kirkley |
| 4,380,998 A | 4/1983 | Kieffer, III et al. |
| 4,406,282 A | 9/1983 | Parker et al. |
| 4,468,218 A | 8/1984 | Armstrong |
| 4,473,073 A | 9/1984 | Darnell |
| 4,552,137 A | 11/1985 | Strauss |
| 4,564,009 A | 1/1986 | Brinkhoff |
| 4,712,537 A | 12/1987 | Pender |
| 4,750,491 A | 6/1988 | Kaufman et al. |
| 4,796,624 A | 1/1989 | Trott et al. |
| 4,800,876 A | 1/1989 | Fox et al. |
| 4,913,132 A | 4/1990 | Gabriel |
| 4,946,440 A | 8/1990 | Hall |
| 4,968,296 A | 11/1990 | Ritch et al. |
| 4,971,076 A | 11/1990 | Densert et al. |
| 5,026,378 A | 6/1991 | Goldsmith, III |
| 5,044,373 A | 9/1991 | Northeved et al. |
| 5,047,007 A | 9/1991 | McNichols et al. |
| 5,053,040 A | 10/1991 | Goldsmith, III |
| 5,092,837 A | 3/1992 | Ritch et al. |
| 5,107,881 A | 4/1992 | Narboni |
| 5,135,478 A | 8/1992 | Sibalis |
| 5,158,540 A | 10/1992 | Wijay |
| 5,178,623 A | 1/1993 | Cinberg et al. |
| 5,254,120 A | 10/1993 | Cinberg et al. |
| 5,261,903 A | 11/1993 | Dhaliwal et al. |
| D352,780 S | 11/1994 | Glaeser et al. |
| 5,370,656 A | 12/1994 | Shevel |
| 5,421,818 A | 6/1995 | Arenberg |
| 5,466,239 A | 11/1995 | Cinberg et al. |
| 5,489,286 A | 2/1996 | Cinberg et al. |
| 5,496,329 A | 3/1996 | Reisinger |
| D378,611 S | 3/1997 | Croley |
| 5,610,988 A | 3/1997 | Miyahara |
| 5,643,280 A | 7/1997 | Del Rio et al. |
| 5,645,584 A | 7/1997 | Suyama |
| 5,658,235 A | 8/1997 | Priest et al. |
| 5,674,196 A | 10/1997 | Donaldson et al. |
| 5,676,635 A | 10/1997 | Levin |
| 5,681,323 A | 10/1997 | Arick |
| D387,863 S | 12/1997 | Herman et al. |
| 5,707,383 A | 1/1998 | Bays et al. |
| 5,775,336 A | 7/1998 | Morris |
| 5,782,744 A | 7/1998 | Money |
| 5,792,100 A | 8/1998 | Shantha |
| 5,827,295 A | 10/1998 | Del Rio et al. |
| 5,893,828 A | 4/1999 | Uram |
| 5,893,837 A | 4/1999 | Eagles et al. |
| 5,984,930 A | 11/1999 | Maciunas et al. |
| D418,223 S | 12/1999 | Phipps et al. |
| D420,741 S | 2/2000 | Croley |
| 6,022,342 A | 2/2000 | Mukherjee |
| 6,024,726 A | 2/2000 | Hill |
| 6,039,748 A | 3/2000 | Savage et al. |
| 6,045,528 A | 4/2000 | Arenberg et al. |
| D424,197 S | 5/2000 | Sydlowski et al. |
| 6,059,803 A | 5/2000 | Spilman |
| D426,135 S | 6/2000 | Lee |
| 6,077,179 A | 6/2000 | Liechty, II |
| 6,110,196 A | 8/2000 | Edwards |
| 6,137,889 A | 10/2000 | Shennib et al. |
| 6,171,236 B1 | 1/2001 | Bonutti |
| 6,183,469 B1 | 2/2001 | Thapliyal et al. |
| 6,200,280 B1 | 3/2001 | Brenneman et al. |
| 6,206,888 B1 | 3/2001 | Bicek et al. |
| 6,245,077 B1 | 6/2001 | East et al. |
| 6,251,121 B1 | 6/2001 | Saadat |
| 6,258,067 B1 | 7/2001 | Hill |
| D450,843 S | 11/2001 | McGuckin, Jr. et al. |
| 6,358,231 B1 | 3/2002 | Schindler et al. |
| 6,398,758 B1 | 6/2002 | Jacobsen et al. |
| 6,416,512 B1 * | 7/2002 | Ellman ............... A61B 18/1485 606/41 |
| 6,440,102 B1 | 8/2002 | Arenberg et al. |
| 6,447,527 B1 | 9/2002 | Gambale et al. |
| 6,475,138 B1 | 11/2002 | Schechter et al. |
| 6,512,950 B2 | 1/2003 | Li et al. |
| 6,514,261 B1 | 2/2003 | Randall et al. |
| 6,520,939 B2 | 2/2003 | Lafontaine |
| 6,522,827 B1 | 2/2003 | Loeb et al. |
| 6,553,753 B1 | 4/2003 | Chang |
| 6,645,173 B1 | 11/2003 | Liebowitz |
| 6,648,873 B2 | 11/2003 | Arenberg et al. |
| 6,663,575 B2 | 12/2003 | Leysieffer |
| 6,682,558 B2 | 1/2004 | Tu et al. |
| 6,770,080 B2 | 8/2004 | Kaplan et al. |
| 6,916,159 B2 | 7/2005 | Rush et al. |
| 6,962,595 B1 | 11/2005 | Chamness et al. |
| 7,127,285 B2 | 10/2006 | Henley et al. |
| 7,137,975 B2 | 11/2006 | Miller et al. |
| D535,027 S | 1/2007 | James et al. |
| 7,160,274 B2 | 1/2007 | Ciok et al. |
| 7,344,507 B2 | 3/2008 | Briggs et al. |
| 7,351,246 B2 | 4/2008 | Epley |
| 7,381,210 B2 | 6/2008 | Zarbatany et al. |
| D595,410 S | 6/2009 | Luzon |
| 7,563,232 B2 | 7/2009 | Freeman et al. |
| D598,543 S | 8/2009 | Vogel et al. |
| 7,654,997 B2 | 2/2010 | Makower et al. |
| 7,677,734 B2 | 3/2010 | Wallace |
| 7,704,259 B2 | 4/2010 | Kaplan et al. |
| 7,749,254 B2 | 7/2010 | Sobelman et al. |
| D622,842 S | 8/2010 | Benoist |
| D640,374 S | 6/2011 | Liu et al. |
| 8,052,693 B2 | 11/2011 | Shahoian |
| 8,192,420 B2 | 6/2012 | Morriss et al. |
| 8,249,700 B2 | 8/2012 | Clifford et al. |
| 8,282,648 B2 | 10/2012 | Tekulve |
| 8,409,175 B2 | 4/2013 | Lee et al. |
| 8,425,488 B2 | 4/2013 | Clifford et al. |
| 8,498,425 B2 | 7/2013 | Graylin |
| 8,518,098 B2 | 8/2013 | Roeder et al. |
| 8,702,722 B2 | 4/2014 | Shahoian |
| 8,840,602 B2 | 9/2014 | Morriss et al. |
| 8,849,394 B2 | 9/2014 | Clifford et al. |
| 8,864,774 B2 | 10/2014 | Liu et al. |
| 8,998,927 B2 | 4/2015 | Kaplan et al. |
| 9,011,363 B2 | 4/2015 | Clopp et al. |
| 9,023,059 B2 | 5/2015 | Loushin et al. |

(56) References Cited

U.S. PATENT DOCUMENTS

| | | |
|---|---|---|
| 9,216,112 B2 | 12/2015 | Clifford et al. |
| 9,320,652 B2 | 4/2016 | Andreas et al. |
| 9,387,124 B2 | 7/2016 | Clifford |
| 9,539,146 B2 | 1/2017 | Girotra et al. |
| 2001/0020173 A1 | 9/2001 | Klumb et al. |
| 2002/0026125 A1 | 2/2002 | Leysieffer |
| 2002/0069883 A1 | 6/2002 | Hirchenbain |
| 2002/0111585 A1 | 8/2002 | Lafontaine |
| 2002/0138091 A1 | 9/2002 | Pflueger |
| 2002/0161379 A1 | 10/2002 | Kaplan et al. |
| 2002/0169456 A1 | 11/2002 | Tu et al. |
| 2003/0018291 A1 | 1/2003 | Hill et al. |
| 2003/0040717 A1 | 2/2003 | Saulenas et al. |
| 2003/0060799 A1 | 3/2003 | Arenberg et al. |
| 2003/0187456 A1 | 10/2003 | Perry |
| 2003/0199791 A1 | 10/2003 | Boecker et al. |
| 2004/0054339 A1 | 3/2004 | Ciok et al. |
| 2004/0064024 A1 | 4/2004 | Sommer |
| 2005/0033343 A1 | 2/2005 | Chermoni |
| 2005/0165368 A1 | 7/2005 | Py et al. |
| 2005/0182385 A1 | 8/2005 | Epley |
| 2005/0187546 A1 | 8/2005 | Bek et al. |
| 2005/0235422 A1 | 10/2005 | Wallace |
| 2005/0240147 A1 | 10/2005 | Makower et al. |
| 2006/0004323 A1 | 1/2006 | Chang et al. |
| 2006/0095050 A1 | 5/2006 | Hartley et al. |
| 2006/0142700 A1 | 6/2006 | Sobelman et al. |
| 2006/0155304 A1 | 7/2006 | Kaplan et al. |
| 2006/0161218 A1 | 7/2006 | Danilov |
| 2006/0163313 A1 | 7/2006 | Larson |
| 2006/0282062 A1 | 12/2006 | Ishikawa et al. |
| 2007/0088247 A1* | 4/2007 | Bliweis .............. A61B 1/00073 604/22 |
| 2007/0233222 A1 | 10/2007 | Roeder et al. |
| 2007/0276466 A1 | 11/2007 | Lavelle et al. |
| 2008/0027423 A1 | 1/2008 | Choi et al. |
| 2008/0051804 A1 | 2/2008 | Cottler et al. |
| 2008/0065011 A1* | 3/2008 | Marchand ............ A61F 2/2433 604/103.02 |
| 2008/0212416 A1 | 9/2008 | Polonio et al. |
| 2008/0262468 A1 | 10/2008 | Clifford et al. |
| 2008/0262508 A1 | 10/2008 | Clifford et al. |
| 2008/0262510 A1 | 10/2008 | Clifford |
| 2009/0163828 A1 | 6/2009 | Turner et al. |
| 2009/0209972 A1 | 8/2009 | Loushin et al. |
| 2009/0299344 A1 | 12/2009 | Lee et al. |
| 2009/0299379 A1 | 12/2009 | Katz et al. |
| 2009/0299433 A1 | 12/2009 | Lee |
| 2010/0041447 A1 | 2/2010 | Graylin |
| 2010/0048978 A1 | 2/2010 | Sing et al. |
| 2010/0061581 A1 | 3/2010 | Soetejo et al. |
| 2010/0198135 A1 | 8/2010 | Morriss et al. |
| 2010/0217296 A1 | 8/2010 | Morriss et al. |
| 2010/0274188 A1 | 10/2010 | Chang et al. |
| 2010/0324488 A1 | 12/2010 | Smith |
| 2011/0015645 A1* | 1/2011 | Liu .................... A61B 17/3468 606/109 |
| 2011/0022069 A1 | 1/2011 | Mitusina |
| 2011/0077579 A1 | 3/2011 | Harrison et al. |
| 2011/0288559 A1 | 11/2011 | Shahoian |
| 2012/0179187 A1 | 7/2012 | Loushin et al. |
| 2012/0265097 A1 | 10/2012 | Melchiorri et al. |
| 2012/0310145 A1 | 12/2012 | Clifford et al. |
| 2013/0030456 A1 | 1/2013 | Assell et al. |
| 2013/0090544 A1 | 4/2013 | Clifford et al. |
| 2013/0338678 A1 | 12/2013 | Loushin et al. |
| 2014/0094733 A1 | 4/2014 | Clopp et al. |
| 2014/0100584 A1 | 4/2014 | Konstorum et al. |
| 2014/0194891 A1 | 7/2014 | Shahoian |
| 2014/0276906 A1 | 9/2014 | Andreas et al. |
| 2014/0277050 A1 | 9/2014 | Andreas et al. |
| 2015/0142029 A1 | 5/2015 | Fahn et al. |
| 2015/0164695 A1 | 6/2015 | Liu et al. |
| 2015/0209509 A1 | 7/2015 | O'Cearbhaill et al. |
| 2015/0305944 A1 | 10/2015 | Kaplan et al. |
| 2016/0038341 A1 | 2/2016 | Clopp et al. |
| 2016/0038342 A1 | 2/2016 | Van et al. |
| 2016/0045369 A1 | 2/2016 | Clopp |
| 2016/0045371 A1 | 2/2016 | Girotra et al. |
| 2016/0213519 A1 | 7/2016 | Andreas et al. |

FOREIGN PATENT DOCUMENTS

| | | |
|---|---|---|
| DE | 19918288 A1 | 10/2000 |
| EP | 0214527 A1 | 3/1987 |
| FR | 2526656 | 11/1983 |
| JP | H 07-116190 A | 5/1995 |
| WO | WO 1999/011175 A1 | 3/1999 |
| WO | WO 2006/119512 | 11/2006 |
| WO | WO 2008/030485 | 3/2008 |
| WO | WO 2008/036368 | 3/2008 |
| WO | WO 2008/131195 | 10/2008 |
| WO | WO 2009/010788 | 1/2009 |
| WO | WO 2011/008948 | 1/2011 |
| WO | WO 2014/075949 | 5/2014 |
| WO | WO 2014/143543 | 9/2014 |
| WO | WO 2014/158571 | 10/2014 |
| WO | WO 2016/022899 | 2/2016 |
| WO | WO 2016/025308 | 2/2016 |
| WO | WO 2016/025309 | 2/2016 |
| WO | WO 2016/025310 | 2/2016 |
| WO | WO 2016/025453 | 2/2016 |

OTHER PUBLICATIONS

U.S. Appl. No. 14/457,412, filed Aug. 12, 2014.
Patent Examination Report No. 1 for Australian Patent Application No. 2013209354, dated Oct. 13, 2014, 5 pages.
First Office Action for Chinese Patent Application No. 200880020861.9, dated Jul. 12, 2011, 10 pages.
Second Office Action for Chinese Patent Application No. 200880020861.9, dated Dec. 31, 2011, 3 pages.
Search Report for Chinese Patent Application No. 201310047126.X, dated Mar. 6, 2015, 2 pages.
Second Office Action for Chinese Patent Application No. 201310047126.X, dated Mar. 16, 2015, 10 pages.
Office Action for European Application No. 08746237.0, dated Mar. 24, 2016, 3 pages.
Office Action for European Application No. 08746237.0, dated Aug. 4, 2015, 7 pages.
Supplementary Partial Search Report for European Application No. 08746237.0, dated Jun. 30, 2014, 9 pages.
Notification of Reasons for Refusal for Japanese Patent Application No. 2010-504267, dated Nov. 20, 2012, 4 pages.
Notification of Reasons for Refusal for Japanese Patent Application No. 2010-504267, dated Nov. 12, 2013, 4 pages.
International Search Report for International Application No. PCT/US2008/060779, dated Sep. 3, 2008.
Written Opinion for International Application No. PCT/US2008/060779, dated Sep. 3, 2008.
International Preliminary Report on Patentability for International Application No. PCT/US2008/060779, dated Nov. 17, 2009.
U.S. Appl. No. 61/085,360, filed Jul. 31, 2008.
International Search Report for International Application No. PCT/US2009/052395, dated Nov. 6, 2009.
Written Opinion for International Application No. PCT/US2009/052395, dated Nov. 6, 2009.
International Search Report for International Application No. PCT/US2010/058718, dated Feb. 17, 2011.
Written Opinion for International Application No. PCT/US2010/058718, dated Feb. 17, 2011.
U.S. Appl. No. 61/225,893, filed Jul. 15, 2009.
Patent Examination Report No. 1 for Australian Application No. 2010273372, dated Nov. 12, 2014, 2 pages.
Office Action for Canadian Application No. 2,768,009, dated Aug. 4, 2016, 4 pages.
First Office Action for Chinese Application No. 201080041755.6, dated Jul. 3, 2013.

(56) References Cited

OTHER PUBLICATIONS

Notification of Reasons for Refusal for Japanese Application No. 2012-520778, dated Feb. 18, 2014.
Communication of the Substantive Examination Report for Mexican Application No. MX/a/2012/000691, dated Apr. 24, 2014.
International Search Report for International Application No. PCT/US2010/042128, dated Aug. 27, 2010.
Written Opinion International Application No. PCT/US2010/042128, dated Aug. 27, 2010.
International Preliminary Report on Patentability for International Application No. PCT/US2010/042128, dated Jan. 17, 2012.
European Search Report for European Application No. 13173409.7, dated Sep. 16, 2013.
International Search Report and Written Opinion for International Patent Application No. PCT/US2015/044179, dated Dec. 18, 2015, 15 pages.
International Search Report and Written Opinion for International Application No. PCT/US2014/018320, dated Jun. 2, 2014, 10 pages.
International Search Report and Written Opinion for International Application No. PCT/US2014/018347, dated Apr. 17, 2014, 9 pages.
International Search Report and Written Opinion for International Application No. PCT/US2015/044173, dated Oct. 12, 2015, 9 pages.
International Search Report and Written Opinion for International Application No. PCT/US2015/044177, dated Oct. 30, 2015, 10 pages.
International Search Report and Written Opinion for International Application No. PCT/US2015/044183, dated Nov. 4, 2015, 9 pages.
International Search Report for International Application No. PCT/US2009/069388, dated Jun. 30, 2010.
Written Opinion for International Application No. PCT/US2009/069388, dated Jun. 30, 2010.
Comeau, M. et al., "Local Anesthesia of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Local Anesthetic," The Larynogoscope, vol. 88, pp. 277-285 (1978).
Echols, D. F. et al., "Anesthesia of the Ear by Iontophoresis of Lidocaine," Arch. Otolaryngol., vol. 101, pp. 418-421 (Jul. 1975).
Epley, J. M., "Modified Technique of Iontophoretic Anesthesia for Myringotomy in Children," Arch. Otolaryngol., vol. 103, pp. 358-360 (Jun. 1977).
Hasegawa, M. et al., "Iontophorectic anaesthesia of the tympanic membrane," Clinical Otolaryngoloy, vol. 3, pp. 63-66 (1978).
Ramsden, R. T. et al., "Anaesthesia of the tympanic membrane using iontophoresis," The Journal of Laryngology and Otology, 56(9):779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.
Medtronic Xomed, "Activent® Antimicrobial Ventilation Tubes," Rev. 1.1, pp. 1-4, 2002, Jacksonville, FL.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.
Armstrong, "A New Treatment for Chronic Secretory Otitis Media" A.M.A. Archives of Otolaryngology, pp. 653-654 (1954).
Feuerstein, "A Split-Tube Prosthesis in Serous Otitis Media" Sixty-ninth Annual Session of the American Academy of Ophthalmology and Otolaryngology, Oct. 18-23, 1964, Chicago, IL, pp. 343-344.
Jurgens. et al., "Three New Middle Ear Ventilation Tubes" Seventy-sixth Annual Session of the American Academy of Ophthalmology and Otolaryngology, Sep. 20-24, 1971, Las Vegas, NV, pp. 1017-1019 (1971).
Lindeman et al., The "Arrow Tube" Residents in Otolaryngology, Massachusetts Eye and Ear Infirmary, 1 page (1964).
Pappas, "Middle Ear Ventilation Tubes" Meeting of the Southern Section of the American Laryngological, Rhinological and Otological Society, Inc., Williamsburg, VA, Jan. 12, 1974, pp. 1098-1117.
Per-Lee, "A Wide Flanged Middle Ear Ventilation Tube" Seventy-first Annual Session of the American Academy of Ophthalmology and Otolaryngology, Oct. 16-21, 1966, Chicago, IL, pp. 358-359.
Reuter, "The Stainless Bobbin Middle Ear Ventilation Tube" Seventy-second Annual Session of the American Academy of Ophthalmology and Otolaryngology, Oct. 29-Nov. 3, 1967, Chicago, IL, pp. 121-122.
Ringenberg, "A New Middle Ear Ventilation Device" Seventy-second Annual Session of the American Academy of Ophthalmology and Otolaryngology, Oct. 29-Nov. 3, 1967, Chicago, IL, 1 page.
Schmidt et al. "Transtympanic Aeration of the Middle Ear With Blocked Eustachian Tube" Acta Otolaryng., pp. 277-282 (1965).
Sheehy, "Collar Button Tube for Chronic Serous Otitis" Sixty-eighth Annual Session of the American Academy of Ophthalmology and Otolaryngology, Oct. 20-25, 1963, New York, NY, pp. 888-889.
Santa Barbara Medco, Inc. "Otological Ventilation Tubes" Product Brochure from http://www.sbmedco.com/ptfe_shepard.asp, 8 pages (Feb. 11, 2001).
Rhinology Products, Boston Medical Products, www.bosmed.com [date of publication unknown], pp. 1-16.

\* cited by examiner

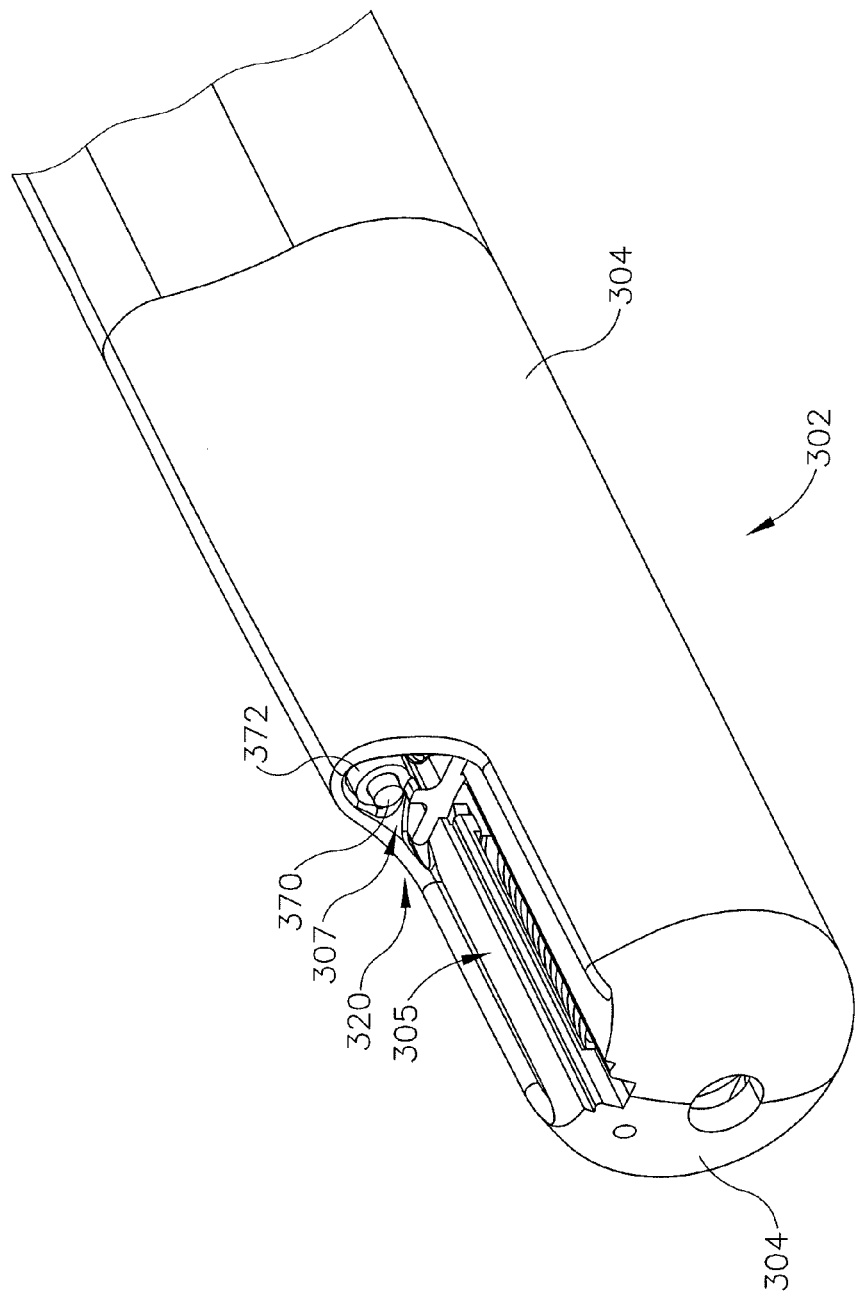

TYMPANOSTOMY TUBE DELIVERY DEVICE WITH REPLACEABLE SHAFT PORTION

BACKGROUND

Some children may exhibit recurrent episodes of otitis media and/or otitis media with effusion. Treatment of severe cases may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane. Pressure equalization tubes may fall out spontaneously within about a year of placement. Exemplary pressure equalization tube delivery systems are disclosed in U.S. Pat. No. 8,052,693, entitled "System and Method for the Simultaneous Automated Bilateral Delivery of Pressure Equalization Tubes," issued Nov. 8, 2011, the disclosure of which is incorporated by reference herein. Additional exemplary pressure equalization tube delivery systems are disclosed in U.S. Pat. No. 8,249,700, entitled "System and Method for the Simultaneous Bilateral Integrated Tympanic Drug Delivery and Guided Treatment of Target Tissues within the Ears," issued Aug. 21, 2012; and U.S. Pub. No. 2011/0015645, entitled "Tympanic Membrane Pressure Equalization Tube Delivery System," published Jan. 20, 2011, the disclosure of which is incorporated by reference herein. Still additional exemplary pressure equalization tube delivery systems are disclosed in U.S. patent application Ser. No. 13/804,553, entitled "Features to Improve and Sense Tympanic Membrane Apposition by Tympanostomy Tube Delivery Instrument," filed Mar. 14, 2013, the disclosure of which is incorporated by reference herein.

Insertion of a pressure equalization tube may be performed using general anesthesia in some cases, which may require additional resources such as an operating room, the presence of an anesthesiologist, and time in a recovery room. Furthermore, the use of general anesthesia may include certain risks that a patient may or may not be comfortable with undertaking. Some pressure equalization tube delivery systems and methods provide a local anesthetic through iontophoresis. Examples of such systems and methods are disclosed in U.S. Pub. No. 2010/0198135, entitled "Systems and Methods for Anesthetizing Ear Tissue," published Aug. 5, 2010, the disclosure of which is incorporated by reference herein. Additional examples of such systems and methods are disclosed in U.S. Pat. No. 8,192,420, entitled "Iontophoresis Methods," issued Jun. 5, 2012, the disclosure of which is incorporated by reference herein.

While a variety of pressure equalization tube delivery systems and methods have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 29B depicts a perspective view of the proximal portion of the PETDD of FIG. 23 with the shaft assembly of FIG. 28 completely disposed within the PETDD.

Figure 1:
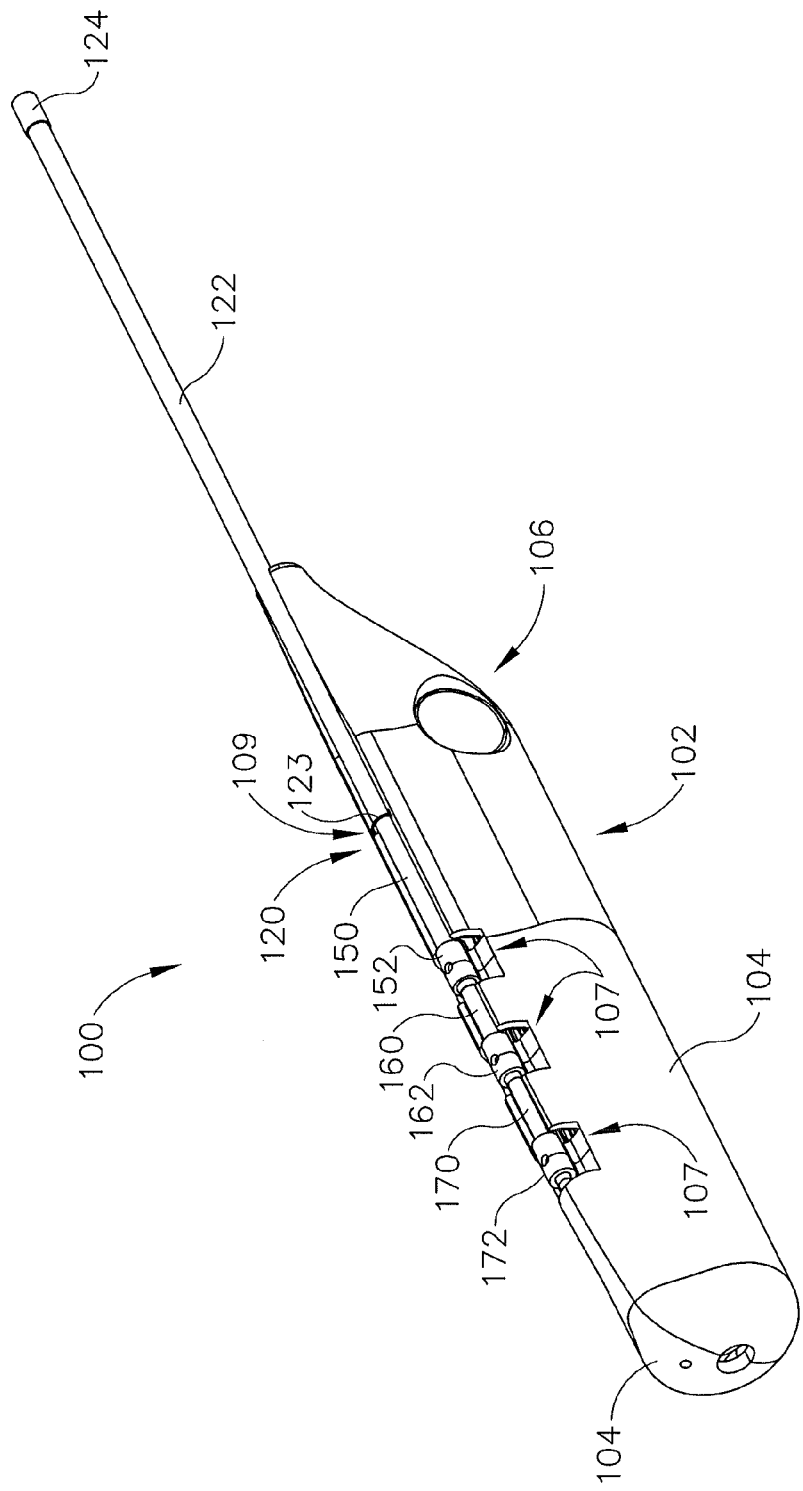
FIG. 1 depicts a perspective view of an exemplary pressure equalization tube delivery device (PETDD)

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Pressure Equalization Tube Delivery Instrument

As noted above, a pressure equalization (PE) tube may be delivered to the tympanic membrane (TM) of a patient as a way of treating, for example, otitis media. In some instances, a delivery instrument may be used to insert PE tubes in the tympanic membrane (TM) without the use of general anesthesia. FIG. 1 shows an exemplary equalization tube delivery device (PETDD) (100) that may be used in such procedures. It should be understood that PETDD (100) may be used with an endoscope to provide visualization of the tympanic membrane (TM) during use of PETDD (100). By way of example only, PETDD (100) may be configured to operate in accordance with at least some of the teachings of U.S. patent application Ser. No. 13/804,553, entitled "Features to Improve and Sense Tympanic Membrane Apposition by Tympanostomy Tube Delivery Instrument," filed Mar. 14, 2013, the disclosure of which is incorporated by reference herein. It should also be understood that a patient may receive local anesthesia at the tympanic membrane (TM) through a process of iontophoresis before PETDD (100) is actuated to deploy a PE tube. By way of example only, such iontophoresis may be provided in accordance with at least some of the teachings of U.S. Pub. No. 2010/0198135, the disclosure of which is incorporated by reference herein; and/or in accordance with at least some of the teachings of U.S. Pat. No. 8,192,420, the disclosure of which is incorporated by reference herein. Other suitable ways in which PETDD (100) may be used will be apparent to those of ordinary skill in the art in view of the teachings herein.

As shown in FIG. 1, PETDD (100) of this example comprises a handpiece (102) and a shaft assembly (120) extending distally from handpiece (102). Hanpdiece (102) is formed by two housing (104) halves that are joined together and that include internal features configured to support various components of PETDD (100). Handpiece (102) is configured to be handheld, such that an operator may fully operate PETDD (100) using a single hand. Shaft assembly (120) of the present example comprises an elongate cannula (122) having a clear tip member (124) at the distal end of cannula (122). Clear tip member (124) is configured to contact a patient's tympanic membrane (TM) while enabling visualization of the distal end of cannula (122). In some versions, tip member (124) is formed of a soft or elastomeric material such as rubber, soft plastic, etc. This may dampen vibrations that might otherwise be transmitted from cannula (122) to the patient's tympanic membrane (TM) during firing of PETDD (100). In addition or in the alternative, tip member (124) may include some other kind of dampening feature as will be apparent to those of ordinary skill in the art in view of the teachings herein.

Figure 3:
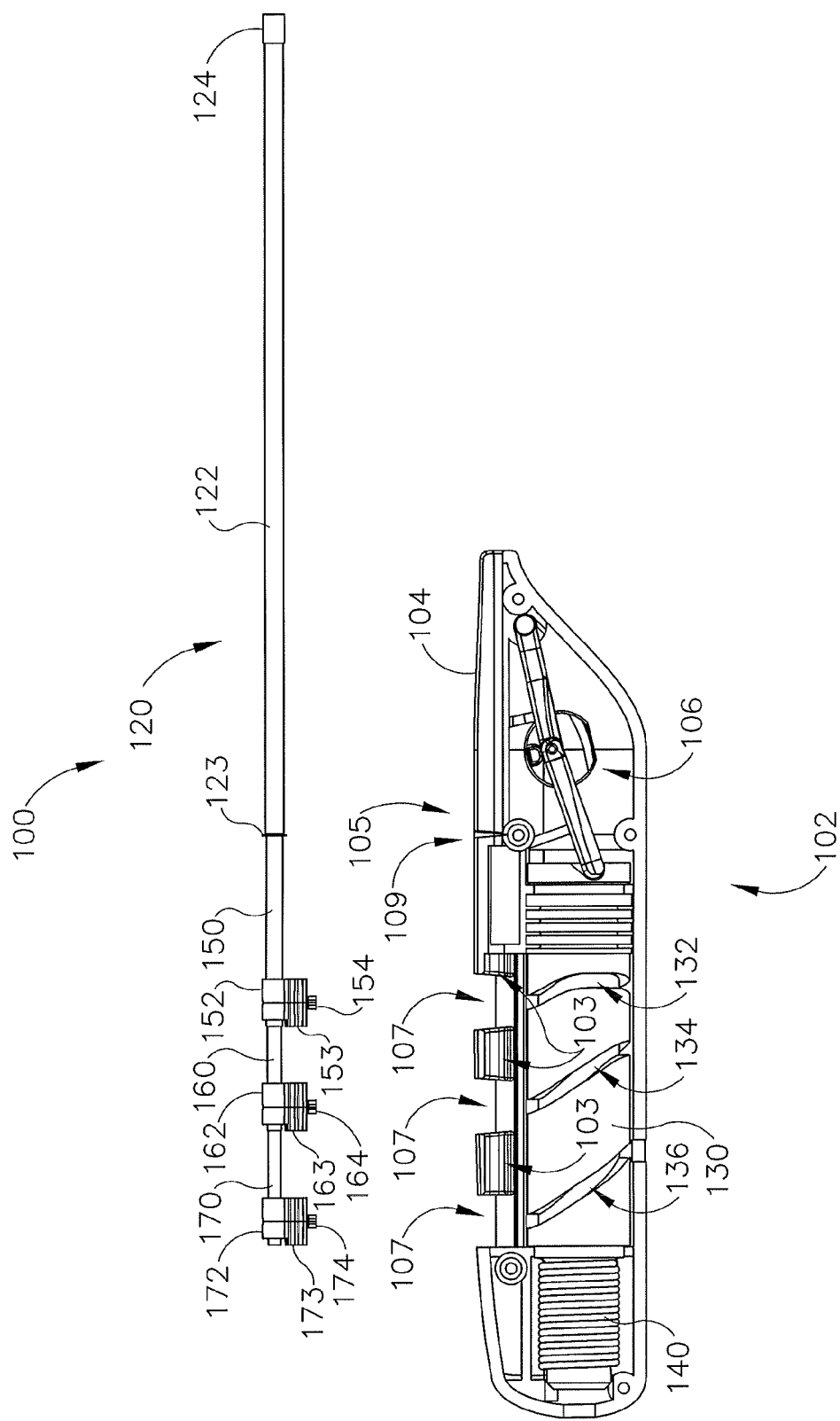
FIG. 3 depicts a partially exploded side elevational view of the PETDD of FIG. 1, with a housing half omitted.

As can be seen in FIGS. 3 and 4, housing (104) supports a camshaft (130) and various other components. Camshaft (130) includes a piercer/dilator track (132), a shield tube track (134), and a pusher track (136). Tracks (132, 134, 136) are formed as recesses in camshaft (130) and each track (132, 134, 136) has a unique configuration in order to provide a particular sequence of operation of translating components. A torsion spring (140) is coupled to the proximal end of camshaft (130). Torsion spring (140) is also grounded against housing (104). Torsion spring (140) resiliently provides a rotational bias to camshaft (130). In particular, torsion spring (140) urges camshaft (130) to rotate in the clockwise direction (viewed from the distal end of PETDD (100) toward the proximal end of PETDD (100)) about the longitudinal axis of camshaft (130). A trigger mechanism (106) selectively resists such rotation. By way of example only, trigger mechanism (106) may be configured to operate in accordance with at least some of the teachings of U.S. patent application Ser. No. 13/804,553, entitled "Features to Improve and Sense Tympanic Membrane Apposition by Tympanostomy Tube Delivery Instrument," filed Mar. 14, 2013; and/or U.S. patent application Ser. No. 14/457,412, entitled "Trigger Assembly for Tympanostomy Tube Delivery Device," filed Aug. 12, 2014, the disclosures of which are incorporated by reference herein. While torsion spring (140) is used to bias camshaft (130) in the present example, it should be understood that any other suitable types of components may be used to bias camshaft (130).

Figure 2:
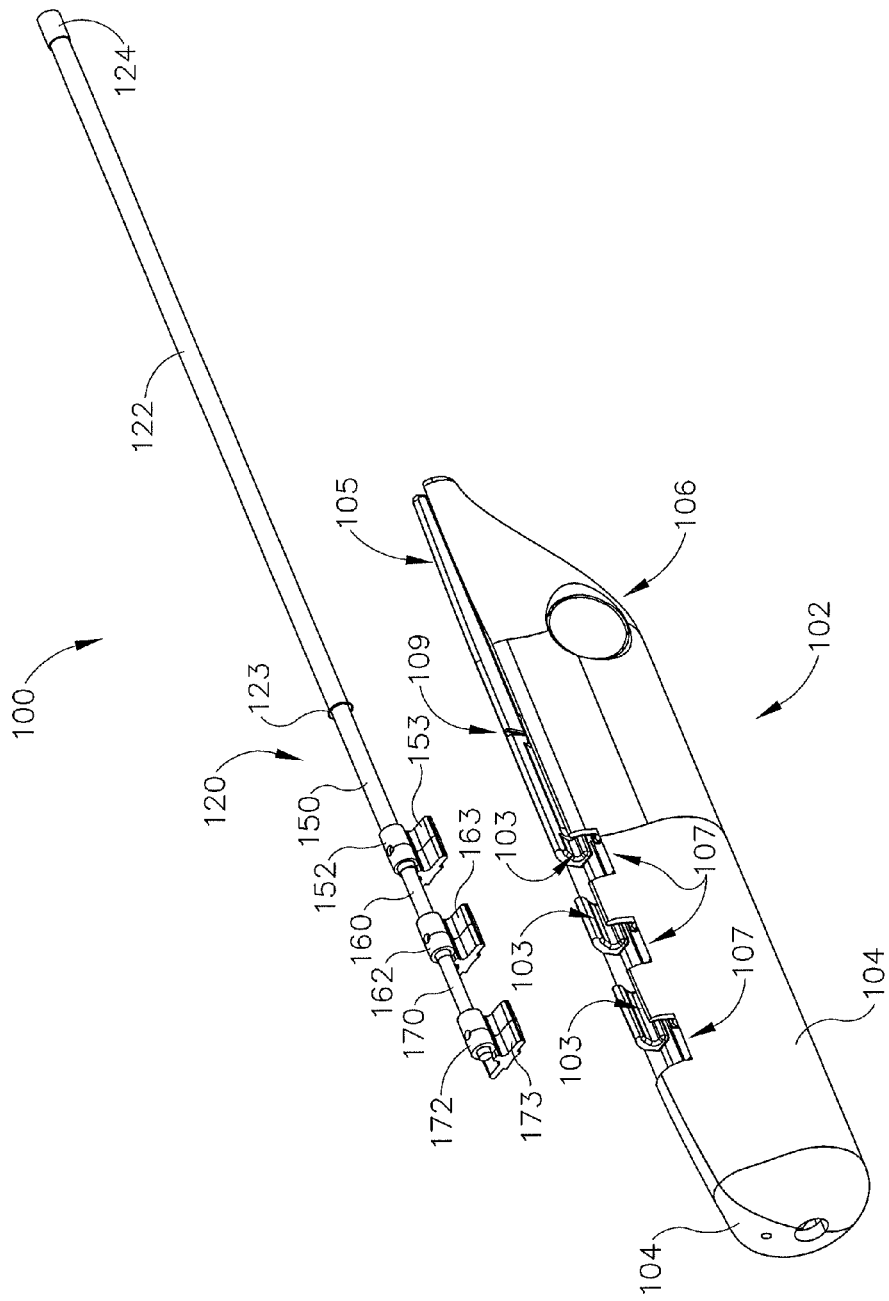
FIG. 2 depicts a partially exploded perspective view of the PETDD of FIG. 1.
Figure 15:
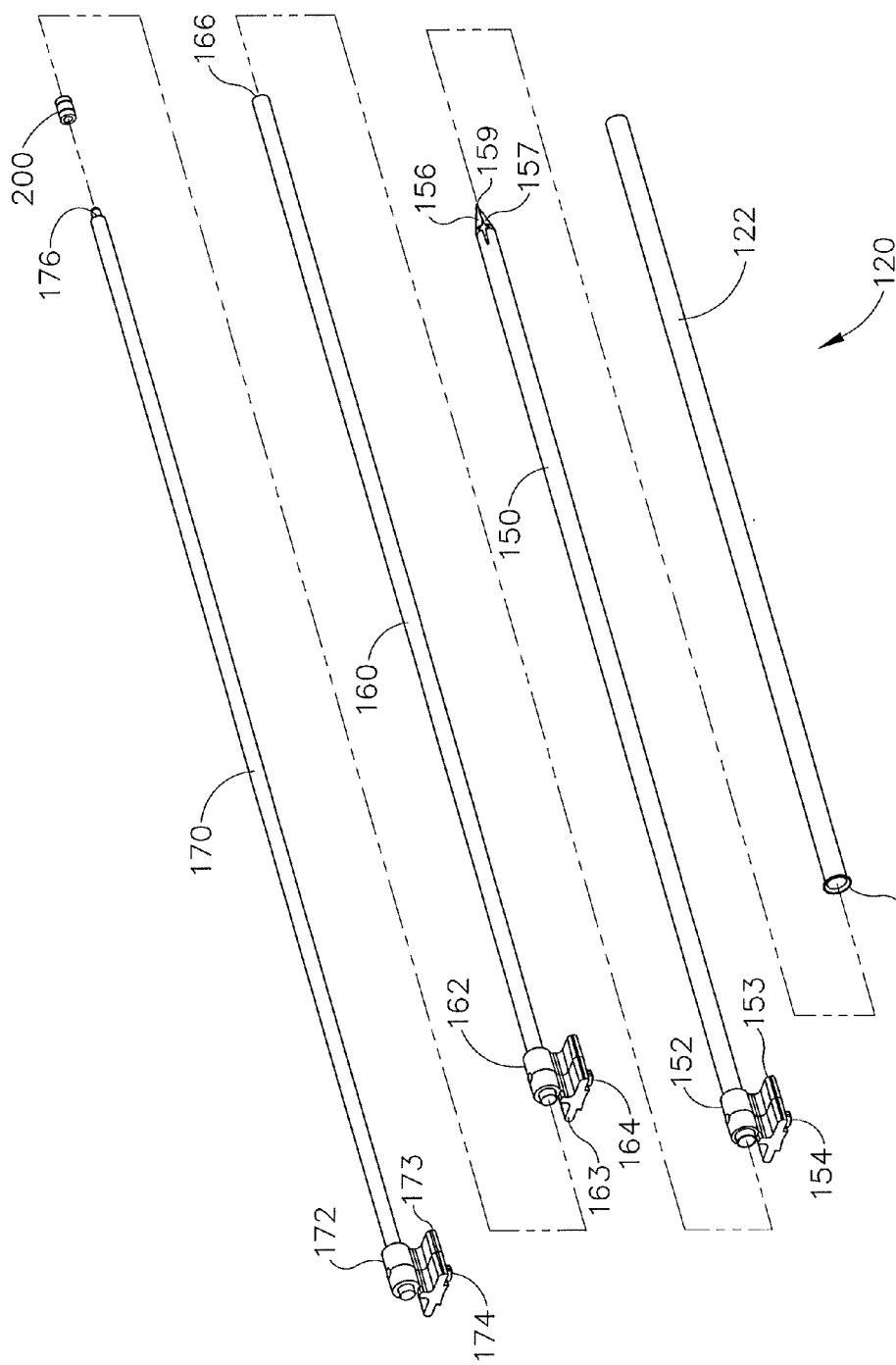
FIG. 15 depicts an exploded perspective view of the shaft assembly of FIG. 4A.

As best seen in FIG. 2, housing halves (104) of handpiece (102) define an elongate channel (105). Housing halves (104) further define a plurality of transverse slots (107) which intersect with channel (105) and thereby provide access to a proximal portion of channel (105). Channel (105) extends longitudinally along handpiece (102) and opens upwardly such that, as will be discussed in more detail below, shaft assembly (120) may be selectively positioned within channel (105). Channel (105) includes a pair of slots (109) formed in opposing interior sidewalls of channel (105). Shaft assembly comprises (120) a piercer/dilator tube (150), a shield tube (160), a pusher tube (170), and cannula (122). Cannula (122) comprises a annular flange (123) extending laterally outwardly from a proximal end of cannula (122). As will be discussed in more detail below, slots (109) of channel (105) are configured to receive annular flange (123) upon insertion of shaft assembly (120) within channel (105) so as to prevent longitudinal translation of cannula (122) relative to handpiece (102). Tubes (150, 160, 170) are all coaxially disposed within cannula (122). As best seen in FIG. 15, pusher tube (170) is coaxially and slidably disposed within shield tube (160), which is coaxially and slidably disposed within piercer/dilator tube (150), which is coaxially and slidably disposed within cannula (122). As will be described in more detail below, tubes (150, 160, 170) all translate relative to cannula (122) in a particular sequence in order to deploy a PE tube (200). This sequence is driven by rotation of camshaft (130).

A cam follower (152) is fixedly secured to the proximal end of piercer/dilator tube (150). Cam follower (152) includes a laterally projecting pin (154) that may be disposed within piercer/dilator track (132), such that rotation of camshaft (130) causes cam follower (152) and piercer/dilator tube (150) to translate. Similarly, a cam follower (162) is fixedly secured to the proximal end of shield tube (160). Cam follower (162) includes a laterally projecting pin (164) that may be disposed within shield tube track (134), such that rotation of camshaft (130) causes cam follower (162) and shield tube (160) to translate. A cam follower (172) is fixedly secured to the proximal end of pusher tube (170). Cam follower (172) includes a laterally projecting pin (174) that may be disposed within pusher tube track (136), such that rotation of camshaft (130) causes cam follower (172) and pusher tube (170) to translate.

Figure 4A:
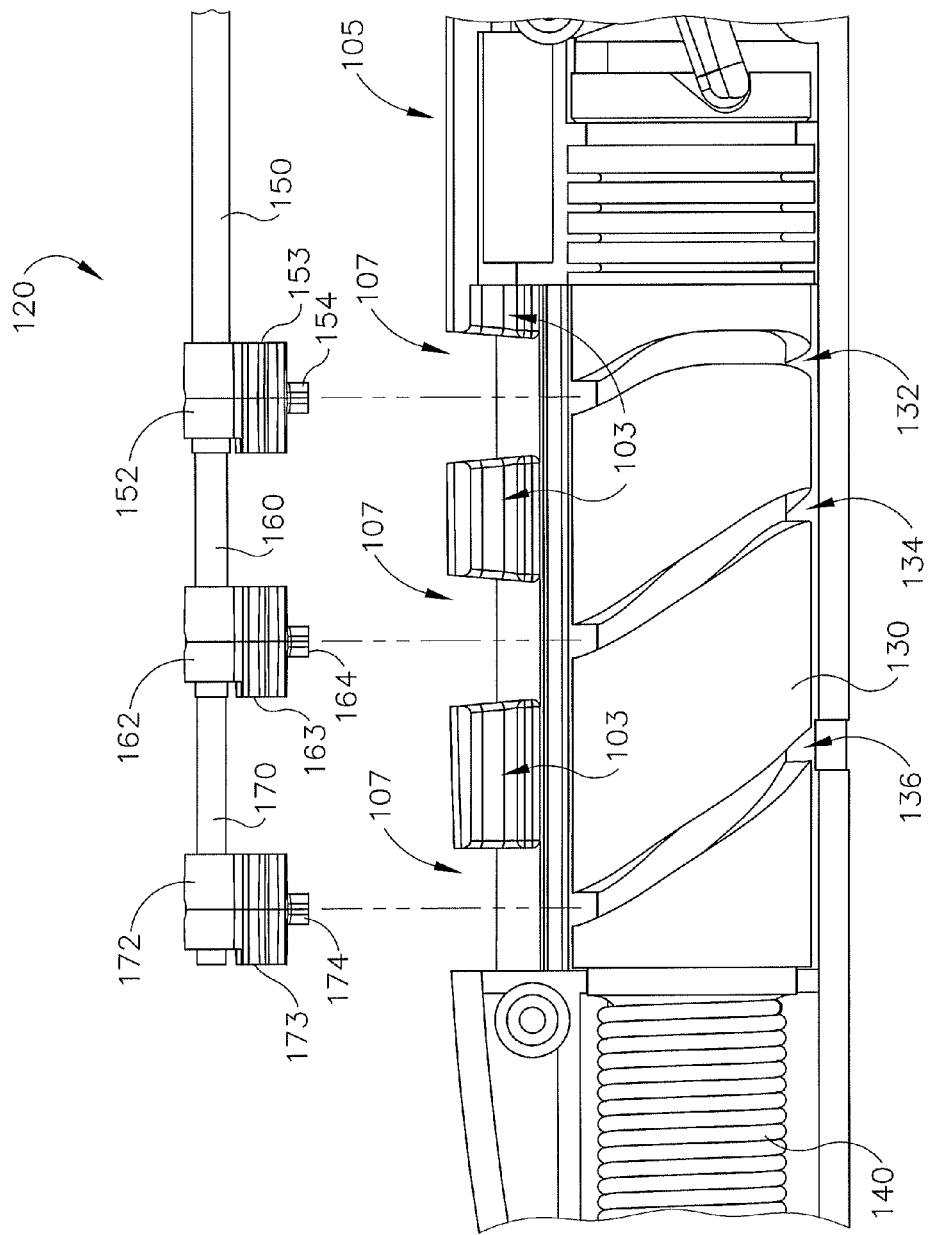
FIG. 4A depicts a side elevational view of a proximal portion of the PETDD of FIG. 1, with a housing half omitted, with a shaft assembly of the PETDD positioned above a handpiece of the PETDD.
Figure 4B:
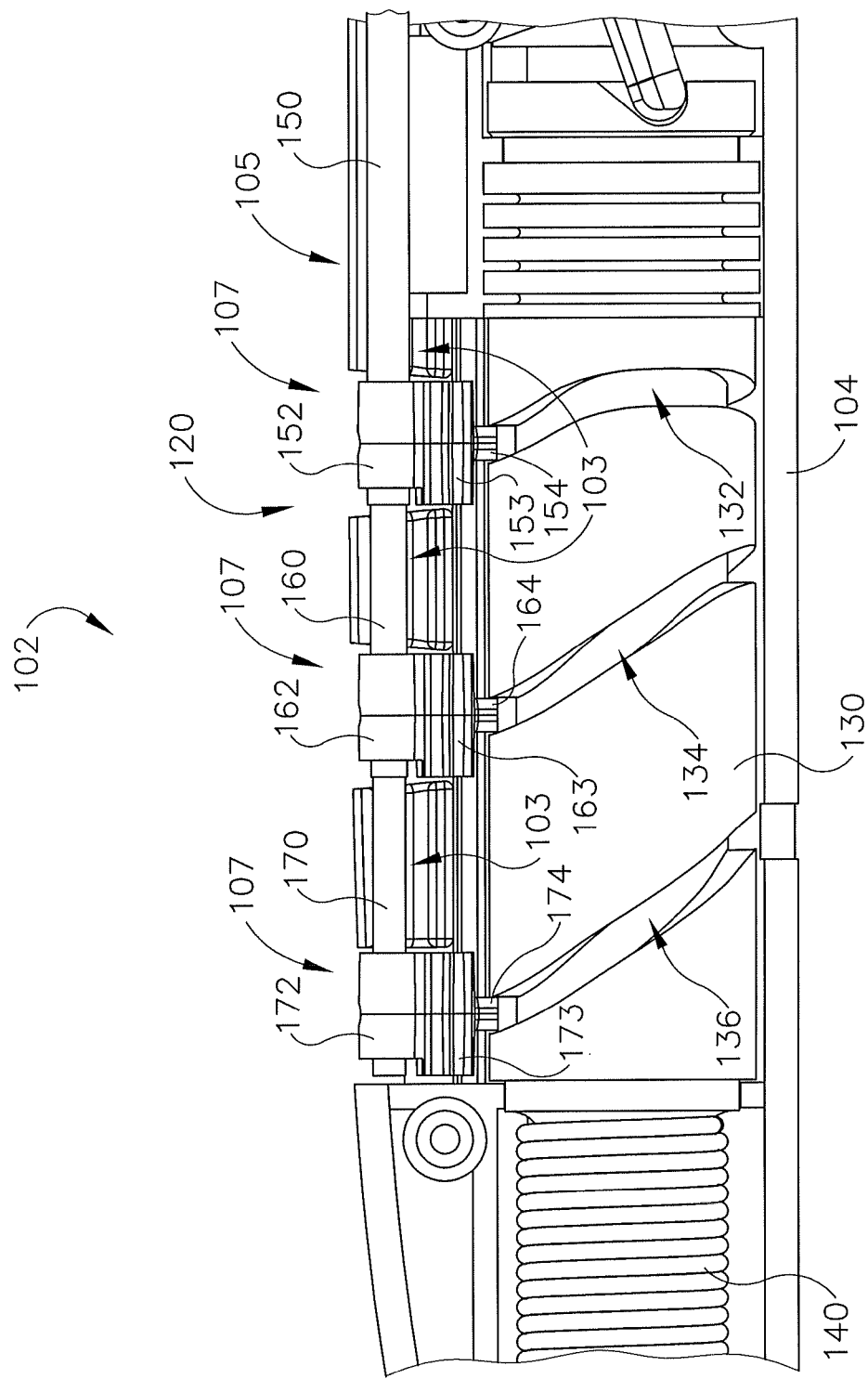
FIG. 4B depicts a side elevational view of a proximal portion of the PETDD of FIG. 1, with a housing half omitted, with the shaft assembly of FIG. 4A positioned within the handpiece of FIG. 4A.
Figure 5:
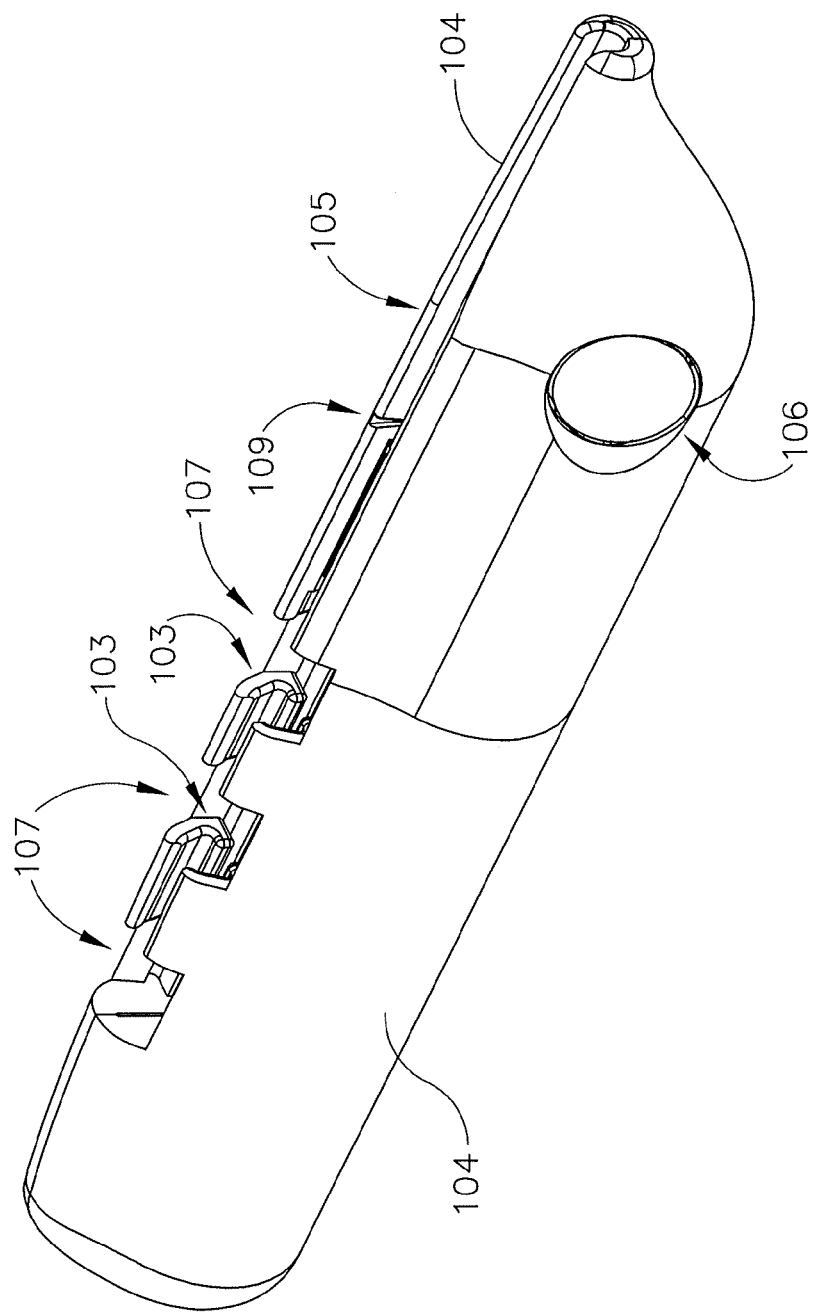
FIG. 5 depicts a perspective view of the handpiece of FIG. 4A.
Figure 6:
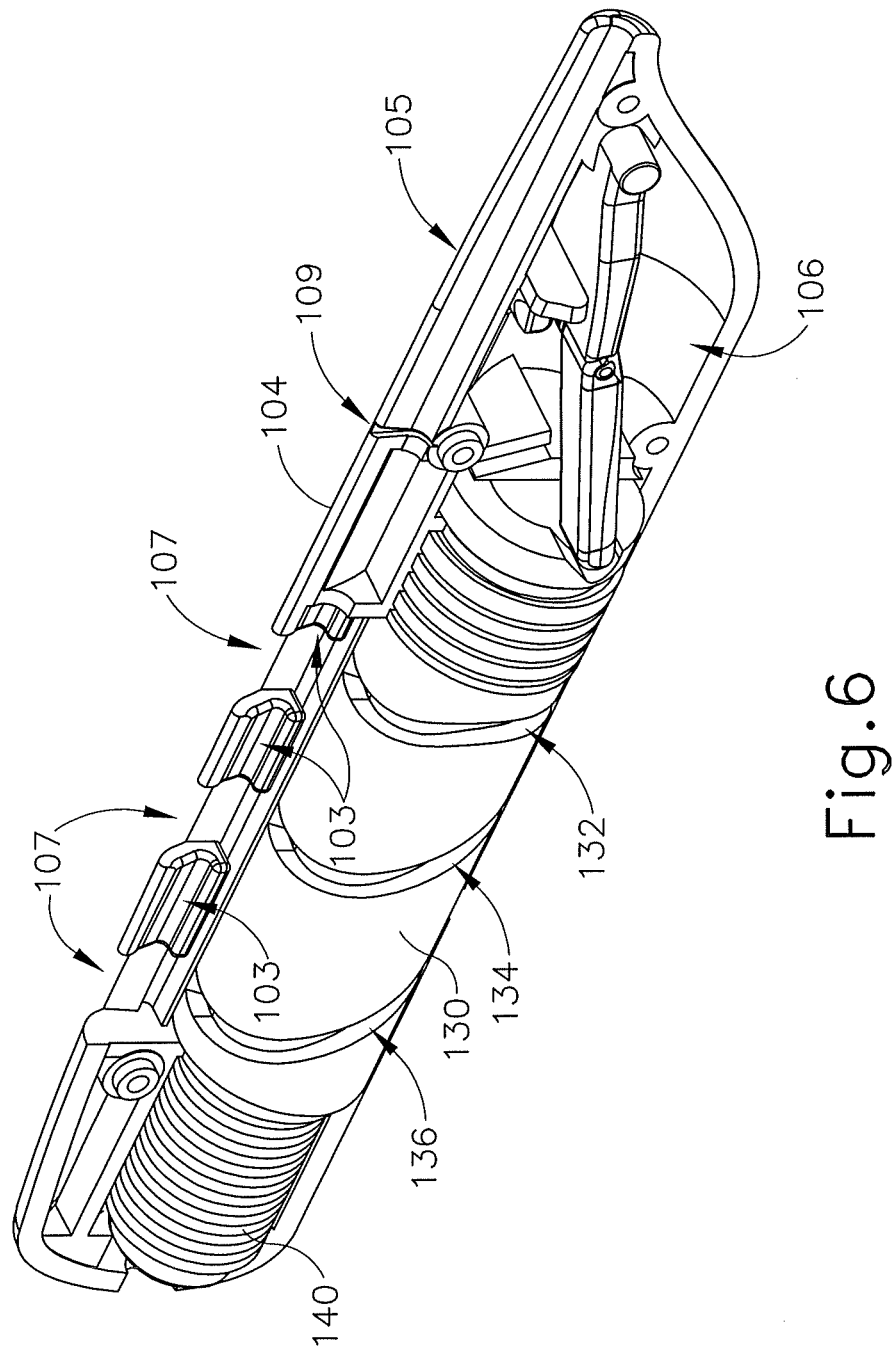
FIG. 6 depicts a perspective view of the handpiece of FIG. 4A, with a housing half omitted.
Figure 7:
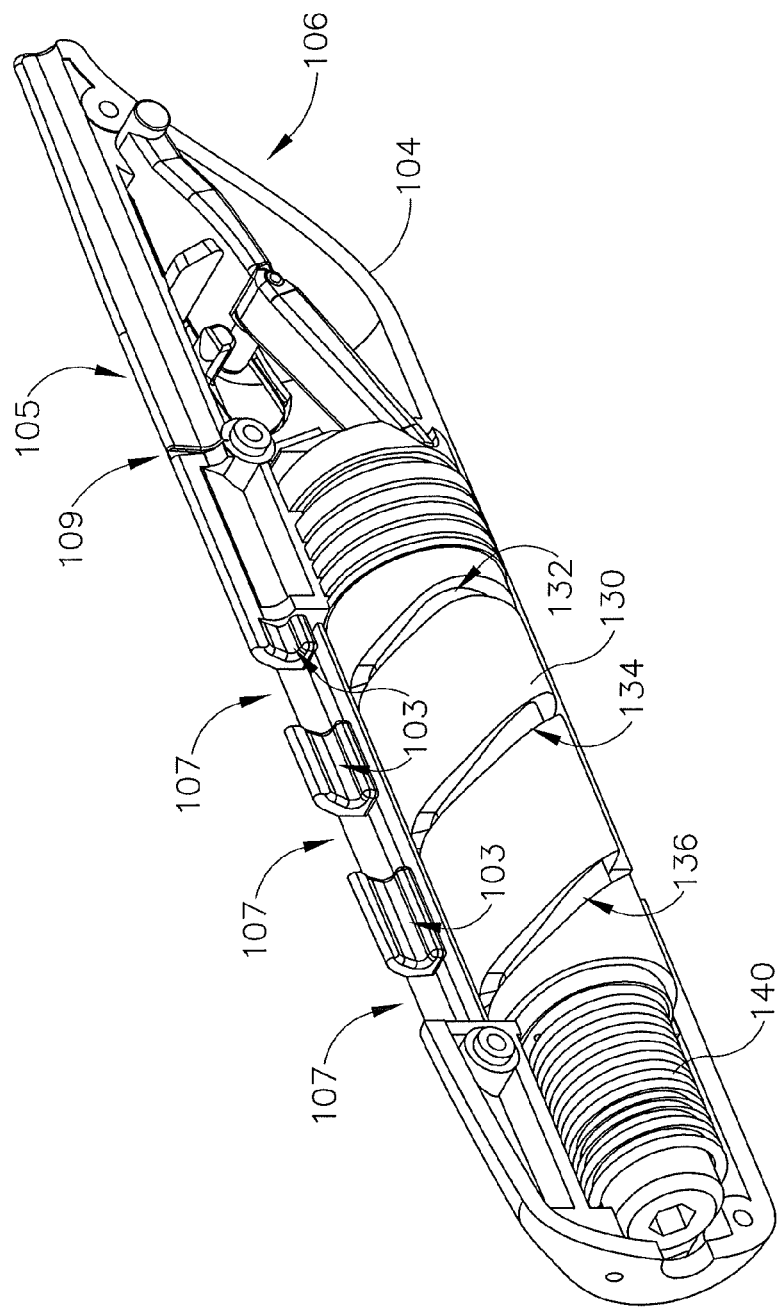
FIG. 7 depicts another perspective view of a handpiece of FIG. 4A, with a housing half omitted.
Figure 8:
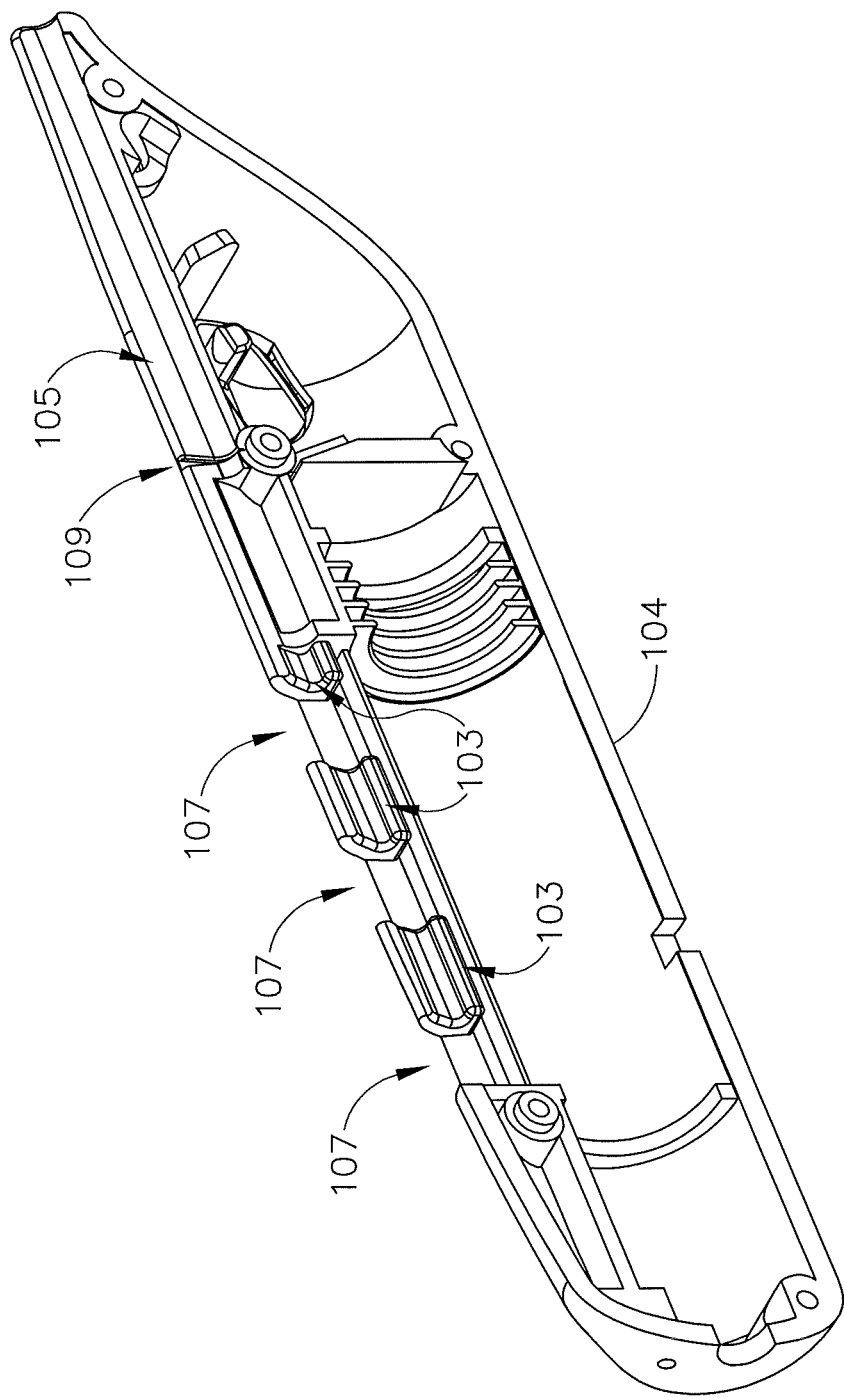
FIG. 8 depicts a perspective view of a housing half of the handpiece of FIG. 4A.
Figure 9:
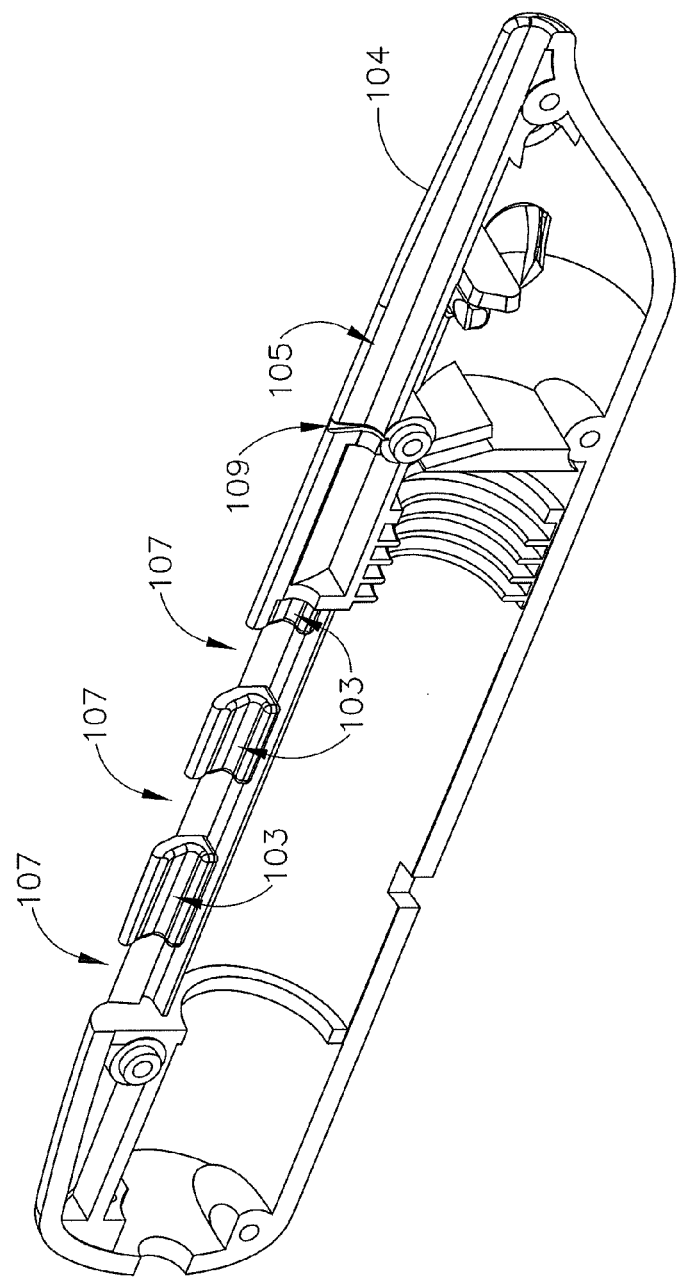
FIG. 9 depicts another perspective view of the housing half of FIG. 8.
Figure 10:
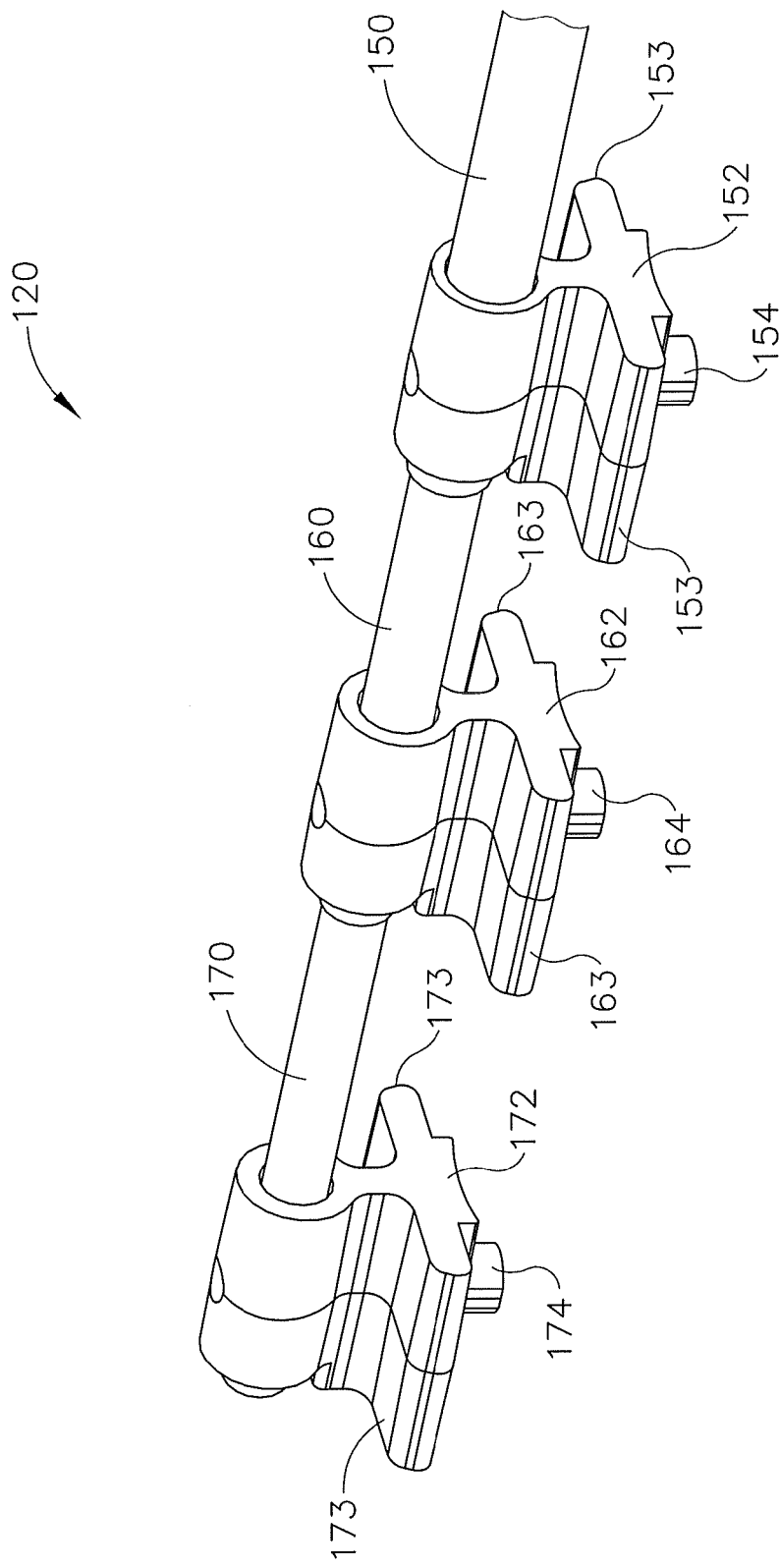
FIG. 10 depicts a perspective view of a proximal portion of the shaft assembly of FIG. 4A.
Figure 11:
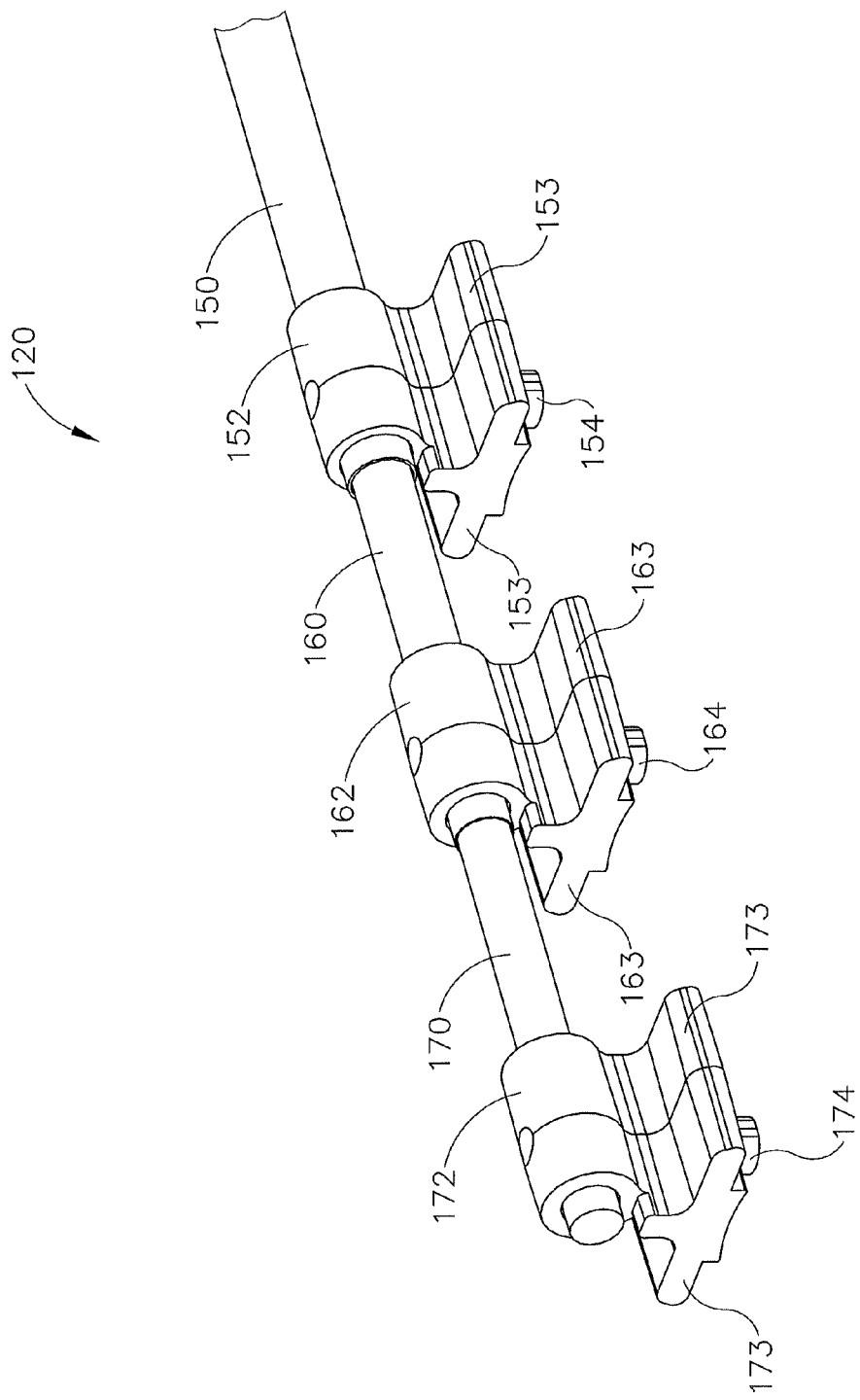
FIG. 11 depicts another perspective view of the proximal portion of the shaft assembly of FIG. 4A.
Figure 12:
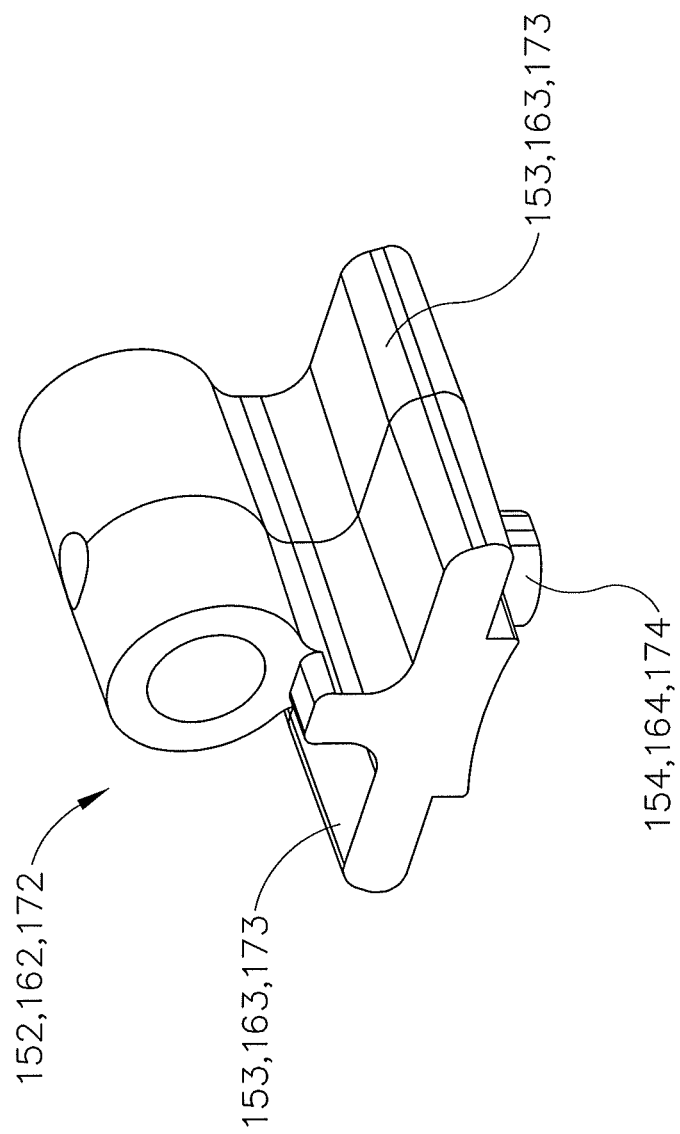
FIG. 12 depicts a perspective view of a follower of the shaft assembly of FIG. 4A.
Figure 13:
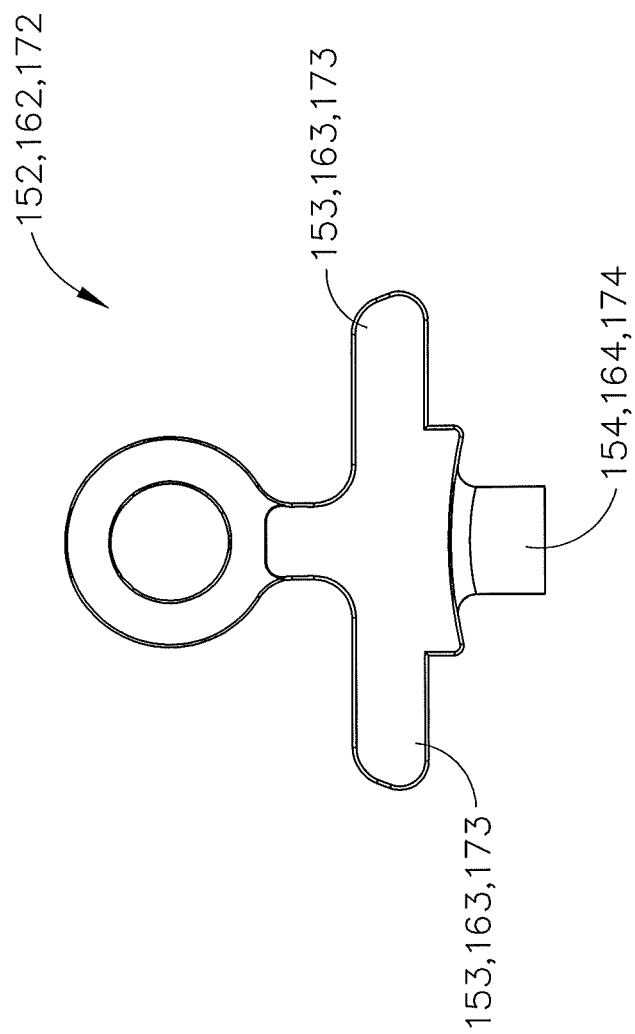
FIG. 13 depicts a front elevational view of the follower of FIG. 12.
Figure 14:
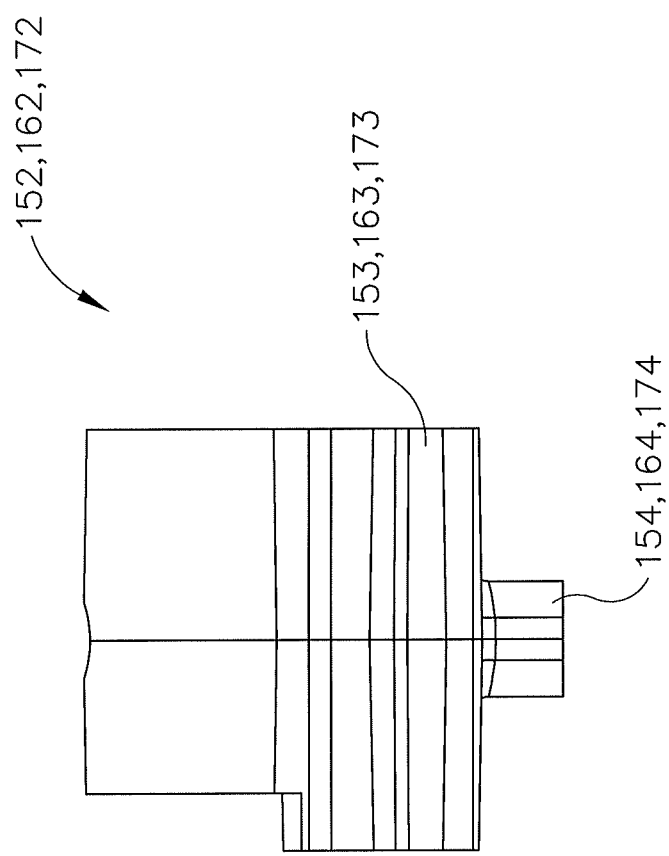
FIG. 14 depicts a side elevational view of the follower of FIG. 12.

As shown in FIGS. 4A and 4B, shaft assembly (120) is selectively coupleable with camshaft (130). Shaft assembly (120) may be coupled with camshaft (130) upon positioning of shaft assembly (120) within channel (105) by moving shaft assembly (120) along a path that is transverse to the longitudinal axis of shaft assembly (120) and the longitudinal axis of handpiece (102). In the present example, camshaft (130) is cocked (i.e. torsion spring (140) is held in tension) when shaft assembly (120) is loaded into handpiece (102), such that during the steps shown in FIGS. 4A and 4B, tracks (132, 134, 136) are positioned to receive corresponding followers (152, 162, 172) of shaft assembly (120). In particular, upon insertion of shaft assembly (120) within channel (105), followers (152, 162, 172) of shaft assembly (120) engage tracks (132, 134, 136) respectively. Further, as shaft assembly (120) is inserted within channel (105), annular flange (123) is positioned within slots (109) of channel (105) so as to prevent longitudinal translation of cannula (122) relative to handpiece (102). Channel (105) includes a longitudinal track (103) formed in opposite sides of channel (105). Track (103) is configured to slidably receive flanges (153, 163, 173) of followers (152, 162, 172) so as to permit longitudinal translation of followers (152, 162, 172) and tubes (150, 160, 170) (see FIGS. 10-15). Thus, it should be appreciated that rotation of camshaft (130) will actuate piercer/dilator tube (150), shield tube (160), and pusher tube (170) via followers (152, 162, 172).

As mentioned above, tubes (150, 160, 170) all translate relative to cannula (122) in a particular sequence in order to deploy PE tube (200) as will be described in greater detail below. This sequence is driven by rotation of camshaft (130). It should be appreciated that channel (105) may be configured such that shaft assembly (120), and in particular cannula (122) of shaft assembly (120), may be coupled within channel (105) in a snap-fit manner. It should further be appreciated that PE tube (200) may be preloaded within shaft assembly (120) before shaft assembly (120) is coupled with handpiece (102). In some versions of shaft assembly (120), shaft assembly (120) may include a frame, bracket, or other feature(s) configured to maintain the relative spacing of cannula (122) and tubes (150, 160, 170) until shaft assembly (120) coupled with handpiece (102). This may ensure that followers (152, 162, 172) of shaft assembly (120) smoothly and properly engage their corresponding tracks (132, 134, 136) upon insertion of shaft assembly (120) in handpiece (102).

Figure 16:
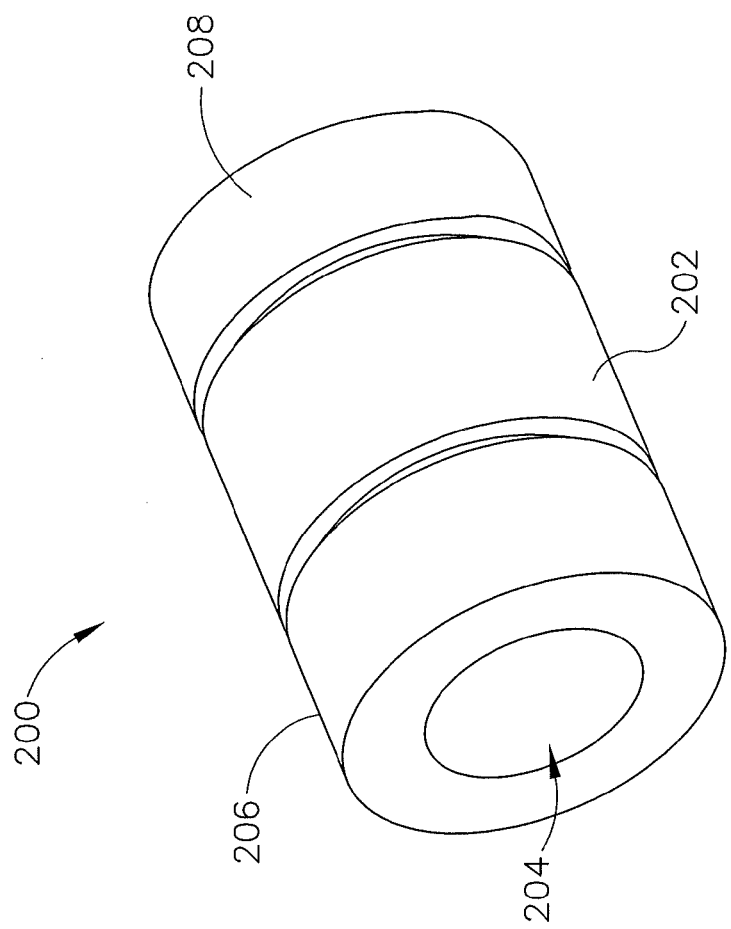
FIG. 16 depicts a perspective view of an exemplary pressure equalization (PE) tube suitable for delivery by the PETDD of FIG. 1, with the PE tube in a compressed state.
Figure 17:
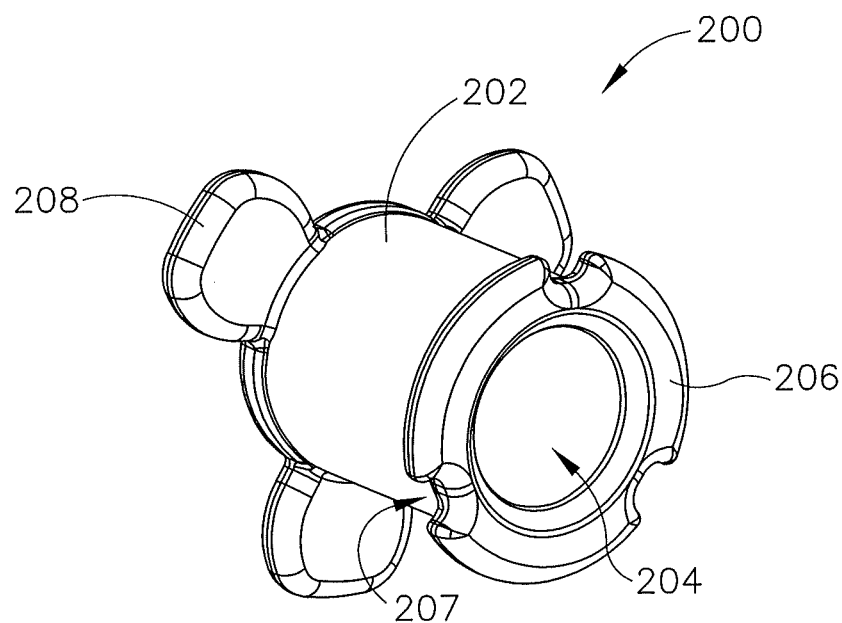
FIG. 17 depicts a perspective view of the proximal side of the PE tube of FIG. 16, with the PE tube in an expanded state.
Figure 18:
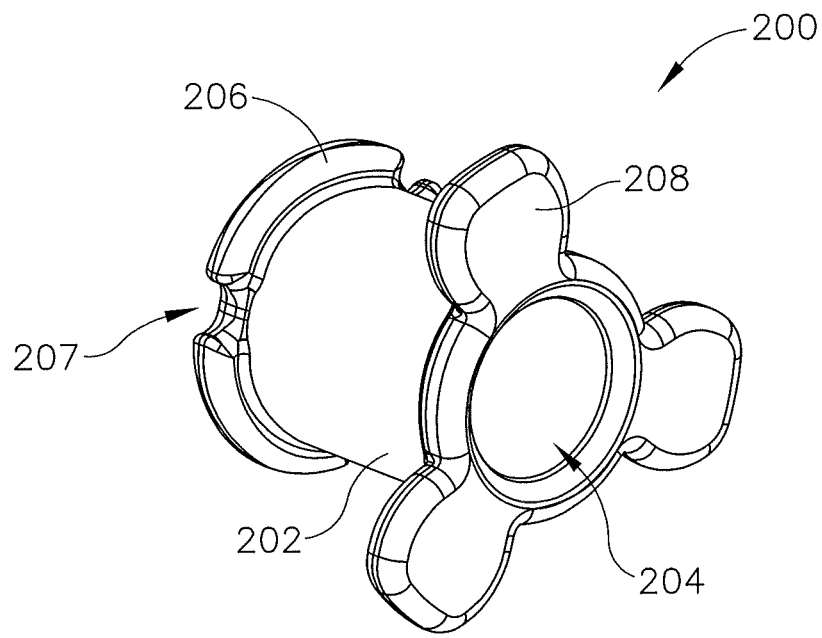
FIG. 18 depicts a perspective view of the distal side of the PE tube of FIG. 16, with the PE tube in an expanded state.
Figure 19:
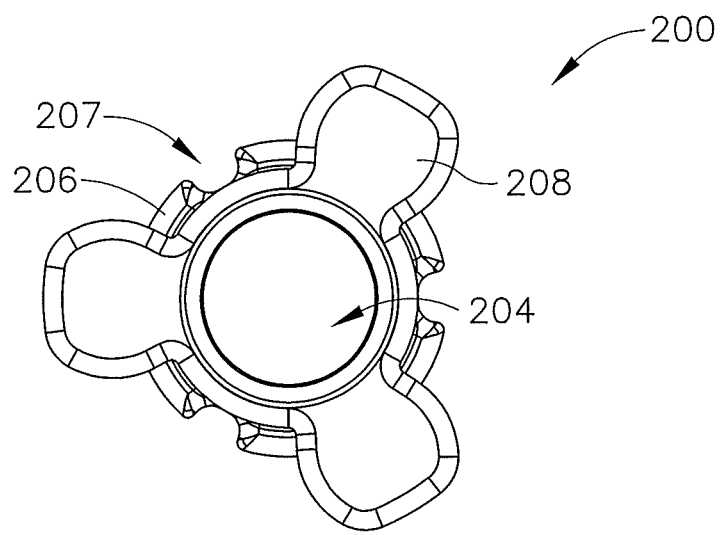
FIG. 19 depicts a distal elevational view of the PE tube of FIG. 16, with the PE tube in an expanded state.
Figure 20:
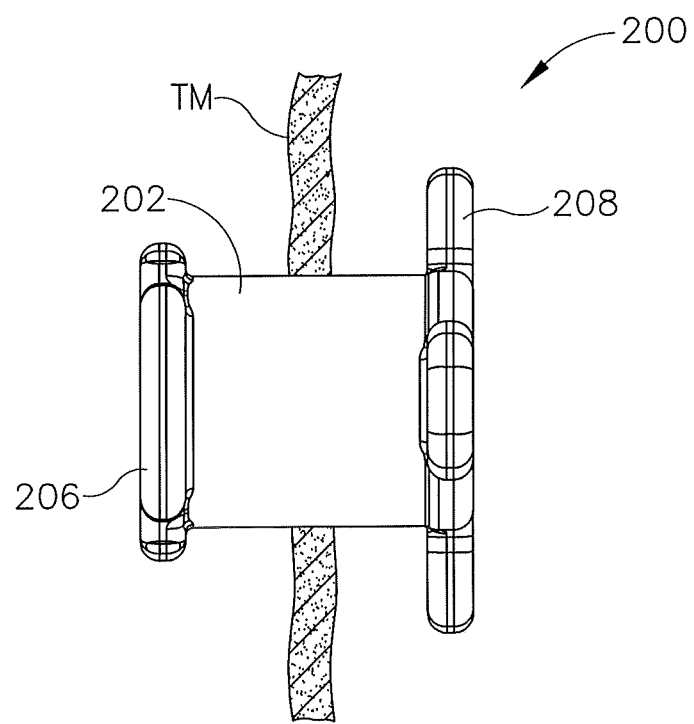
FIG. 20 depicts a side elevational view of the PE tube of FIG. 16 positioned within a tympanic membrane, with the PE tube in an expanded state.

FIGS. 16-20 show an exemplary PE tube (200) in greater detail. PE tube (200) of this example includes a cylindraceous body (202) that defines a passageway (204). A flange (206) is located at the proximal end of body (202) while a set of petals (208) are located at the distal end of body (202). (Prior to being deployed, PE tube (200) is disposed within shield tube (160) in a "compressed" state as shown in FIG. 16 thereby assuming a generally cylindraceous configuration. After being deployed, PED expands into an "expanded" state as shown in FIGS. 17-20.) Flange (206) includes a plurality of inwardly directed recesses (207). Recesses (207) are configured to facilitate flexing of flange (206) from an outwardly extended position to a generally cylindraceous position where the material forming flange (206) extends longitudinally. While three recesses (207) are shown, it should be understood that any other suitable number of recesses (207) may be provided. Similarly, while three petals (208) are shown, it should be understood that any other suitable number of petals (208) may be provided.

PE tube (200) is formed of a resilient material that is biased to assume the rivet like configuration shown in FIGS. 17-20. However, flange (206) and petals (208) may be flexed inwardly toward the longitudinal axis of body (202) to provide PE tube (200) with a cylindraceous configuration. In particular, flange (206) and petals (208) may be flexed such that their outer surfaces are at the same radial distance from the longitudinal axis as the outer perimeter of body (202).

This radial distance may be slightly less than the radial distance associated with the inner diameter of shield tube (160), such that PE tube (200) may collapse to fit within shield tube (160). When PE tube (200) is disposed in a tympanic membrane (TM), petals (208) are located medially (i.e., on the middle ear side) while flange (206) is located laterally (i.e., on the outer ear side). By way of example only, PE tube (200) may also be configured in accordance with at least some of the teachings of U.S. patent application Ser. No. 13/800,113, entitled "Tympanic Membrane Pressure Equalization Tube," filed on Mar. 13, 2013, the disclosure of which is incorporated by reference herein. Other suitable forms that PE tube (200) may take will be apparent to those of ordinary skill in the art in view of the teachings herein.

Figure 21:
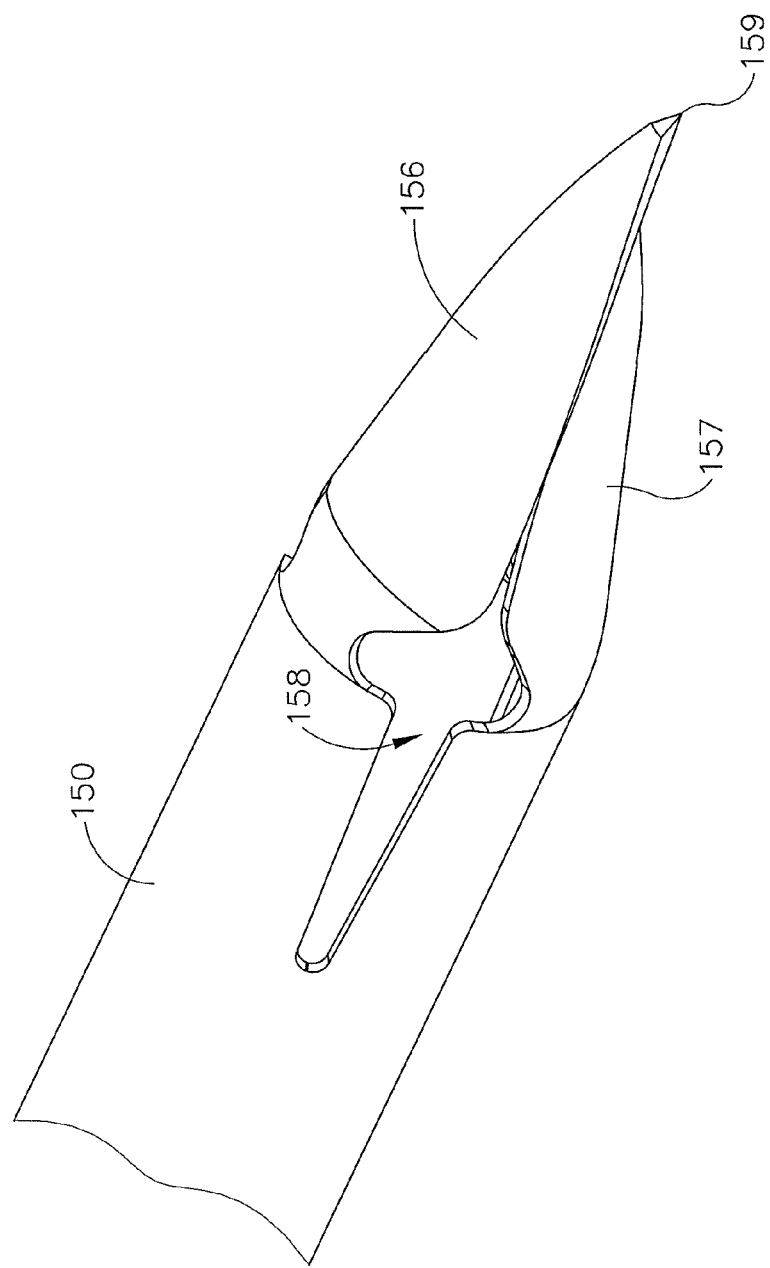
FIG. 21 depicts a perspective view of a distal end of a piercer/dilator tube of the shaft assembly of FIG. 4A.

As shown in FIG. 21, a distal end of piercer/dilator tube (150) includes a plurality of generally flexible leaves (156, 157) that are separated by longitudinally extending gaps (158). By way of example only, piercer/dilator tube (150) may be configured and operable in accordance with at least some of the teachings of U.S. patent application Ser. No. 13/804,612, entitled "Tympanostomy Tube Delivery Device with Cutting Dilator," filed Mar. 14, 2013, the disclosure of which is incorporated by reference herein. Leaves (156, 157) are resiliently biased to assume the inwardly deflected positioning shown in FIG. 21; but are operable to flex outwardly from this positioning as will be described in greater detail below. Also as shown in FIG. 21, the distal end of leaf (156) of piercer/dilator tube (150) includes a sharp, multi-faceted piercer tip (159) that is configured to pierce through a patient's tympanic membrane (TM). As shown in FIGS. 15 and 22A-22G, a distal end of shield tube (160) simply includes a circular edge (166). A distal end of pusher tube (170) includes a cylindrical projection (176) configured to be disposed within passageway (204) of PE tube (200).

Figure 22A:
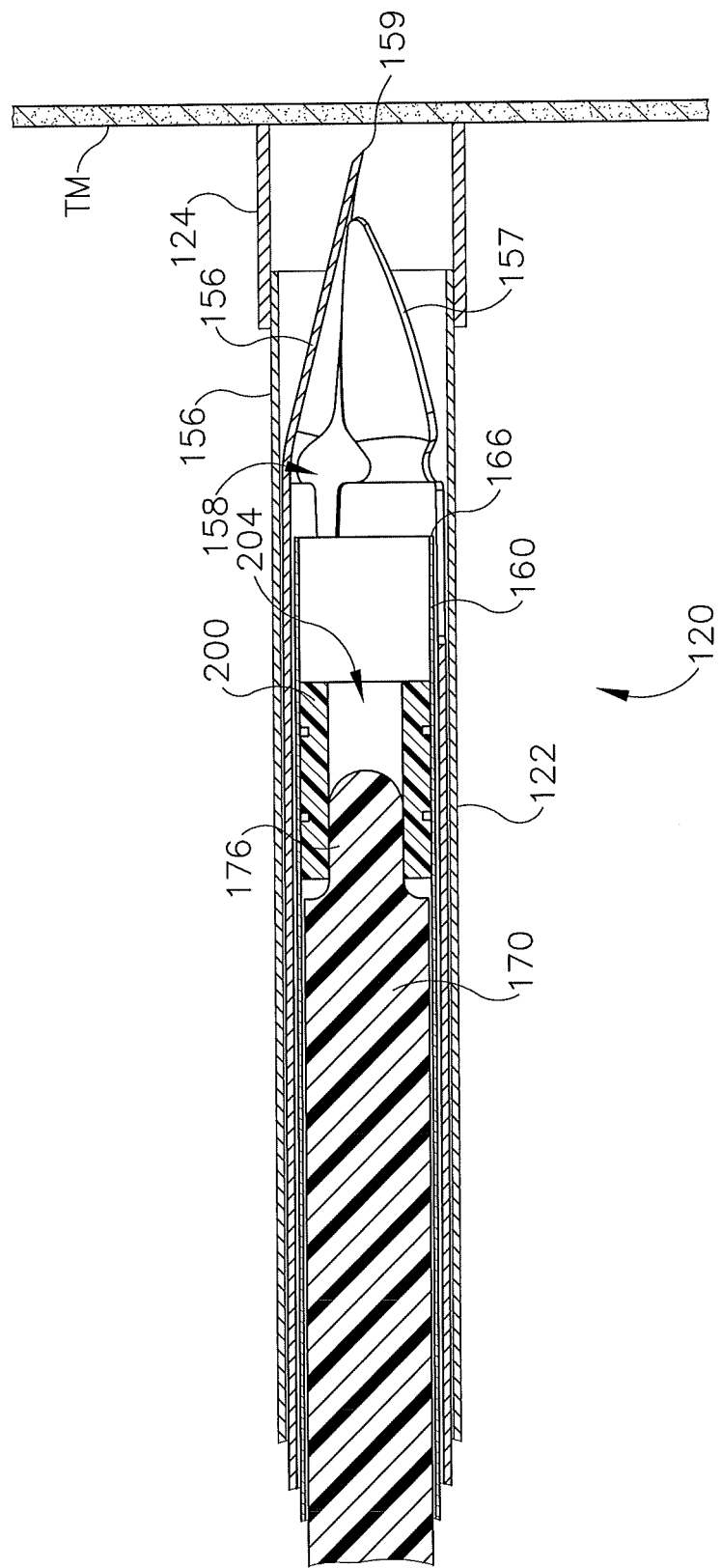
FIG. 22A depicts a cross-sectional side elevational view of a distal end of the shaft assembly of FIG. 4A engaged with a tympanic membrane.

FIG. 22A shows the positioning of tubes (150, 160, 170) and PE tube (200) within cannula (120) before camshaft (130) starts rotating from a home position. As shown, the distal edge of tip member (124) is in apposition with tympanic membrane (TM). As also shown, shield tube (160) is positioned proximally to leaves (156, 157) of dilator tube (150), such that leaves (156, 157) are in the inwardly deflected position. PE tube (200) is positioned within the distal end of shield tube (160), whose distal edge (166) is just proximal to leaves (156, 157). Pusher tube (170) is proximal to PE tube (200), with cylindrical projection (176) of pusher tube (170) disposed within passageway (204) of PE tube (200). In the present example, PE tube (200) is resiliently biased to assume a rivet-like shape presenting transverse petals (208) and a flange (206) (see FIGS. 17-20). However, as mentioned above, PE tube (200) is compressed against this bias, thereby assuming the generally cylindraceous configuration, when PE tube (200) is disposed within shield tube (160) as shown in FIG. 22A.

Figure 22B:
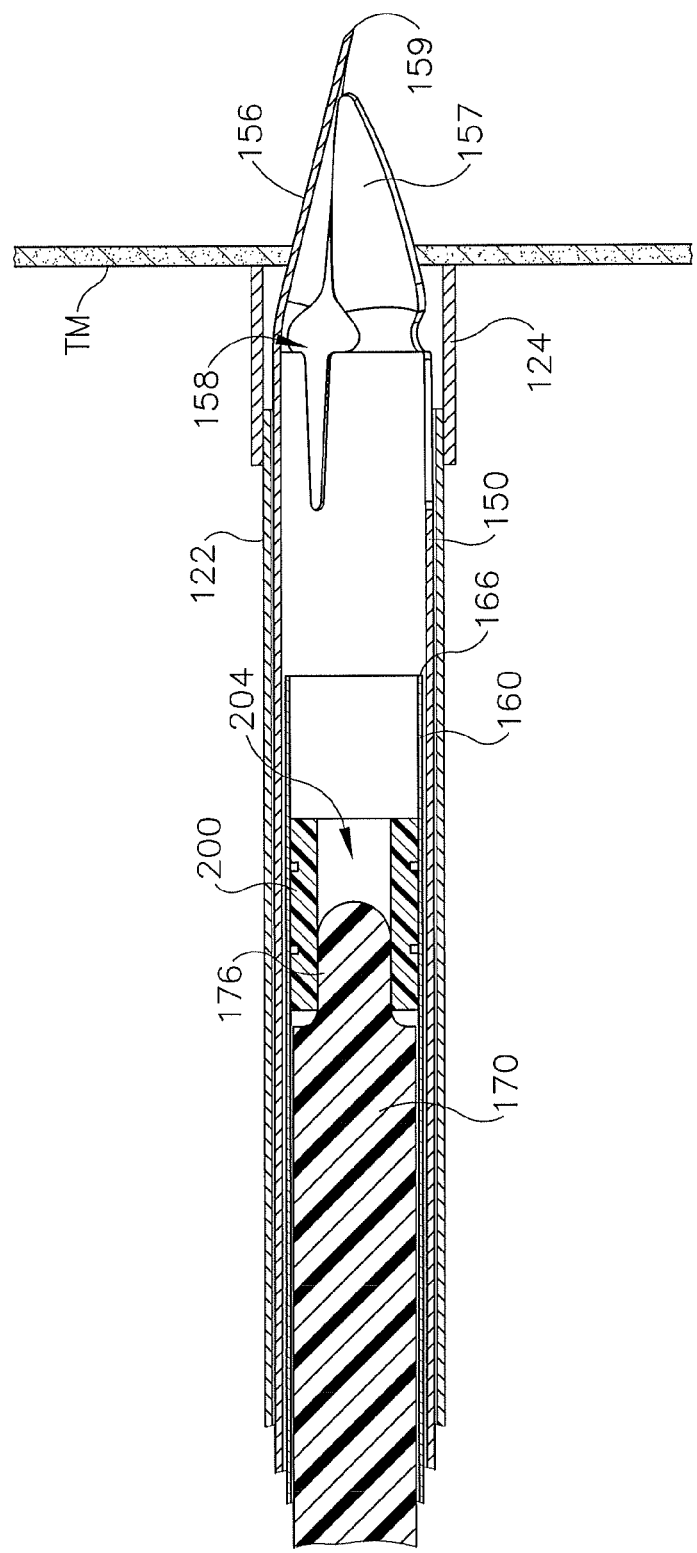
FIG. 22B depicts a cross-sectional side elevational view of the distal end of the shaft assembly of FIG. 4A engaged with a tympanic membrane, with the piercer/dilator tube of FIG. 21 driven distally through the tympanic membrane.
Figure 22C:
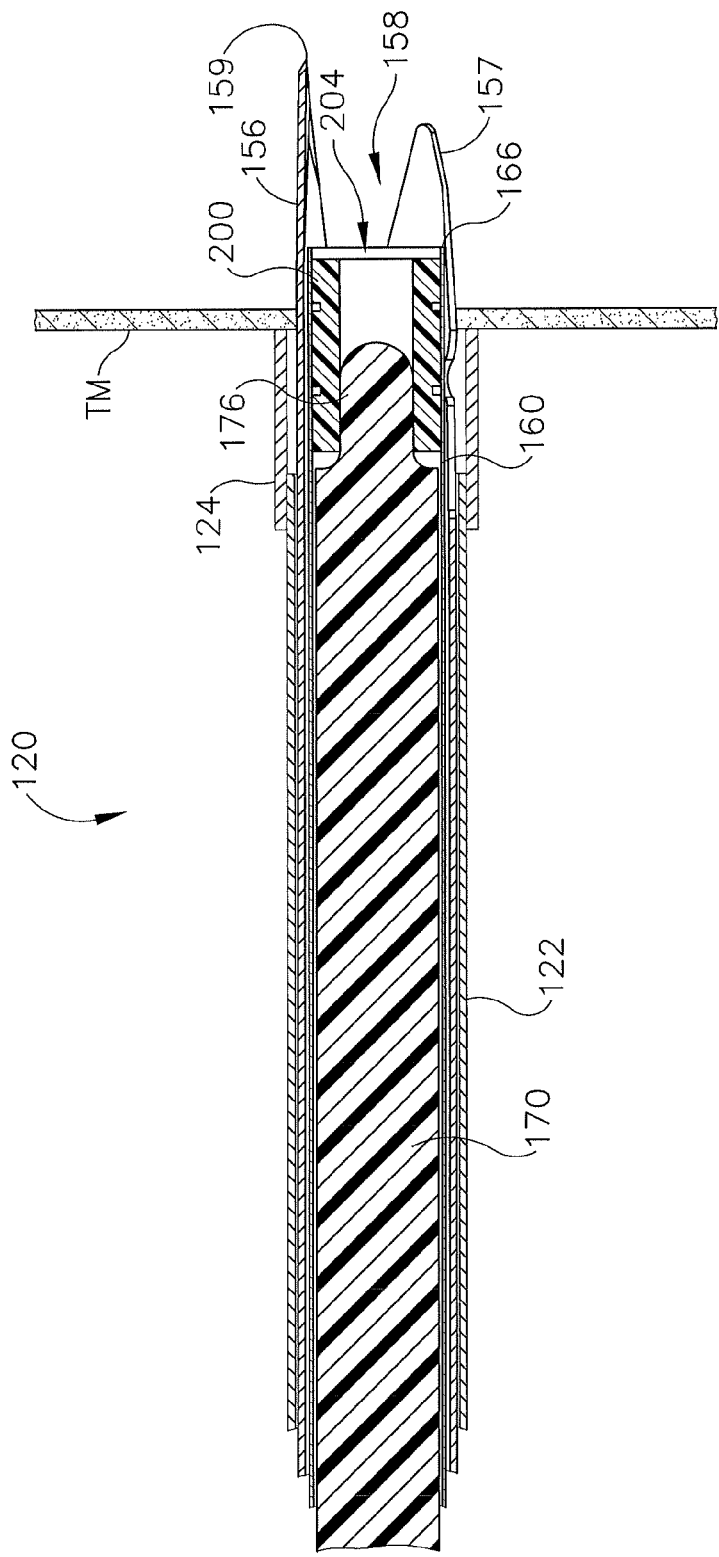
FIG. 22C depicts a cross-sectional side elevational view of the distal end of the shaft assembly of FIG. 4A engaged with a tympanic membrane, with a shield tube, a plunger, and the PE tube of FIG. 20 driven distally so as to drive leaves of the piercer/dilator tube of FIG. 21 outwardly within the tympanic membrane.
Figure 22D:
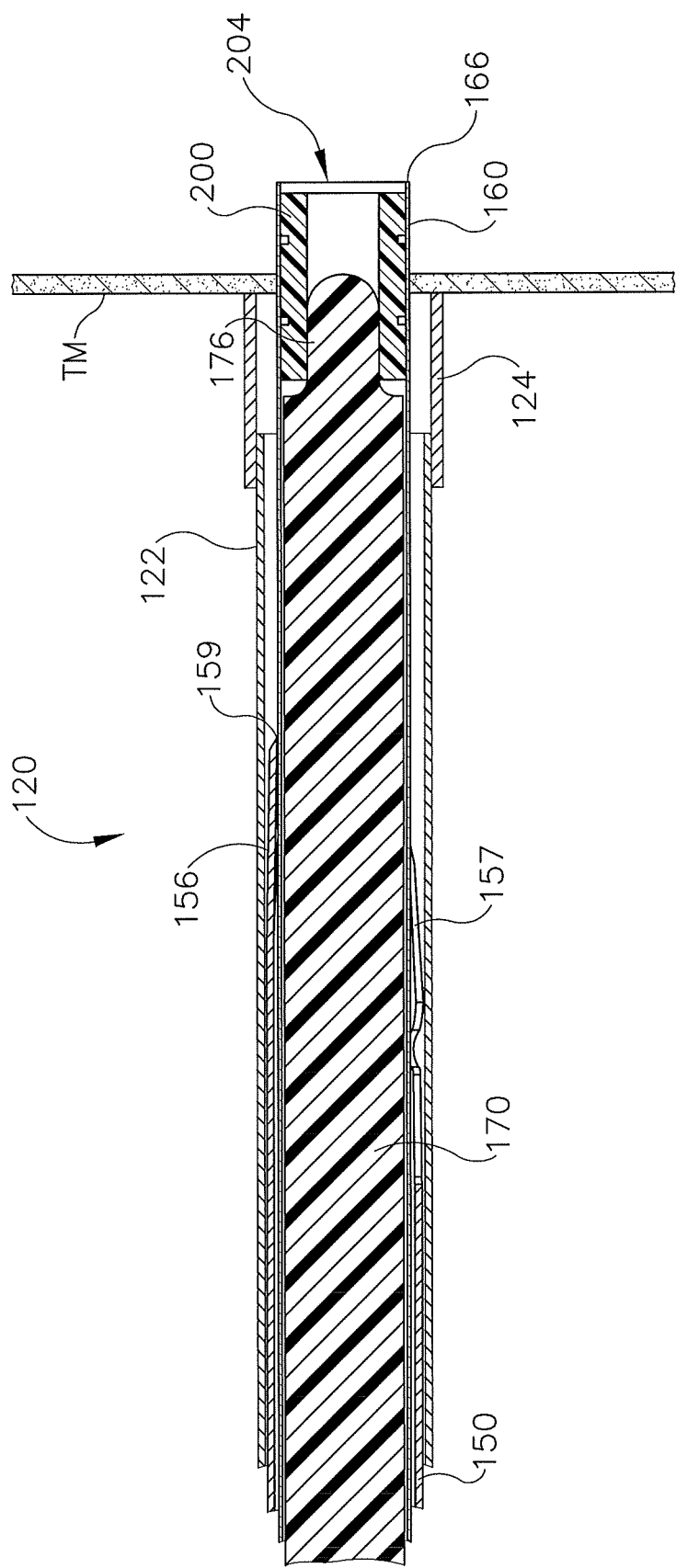
FIG. 22D depicts a cross-sectional side elevational view of the distal end of the shaft assembly of FIG. 4A engaged with a tympanic membrane, with the piercer/dilator tube of FIG. 21 retracted proximally within the shaft assembly.
Figure 22E:
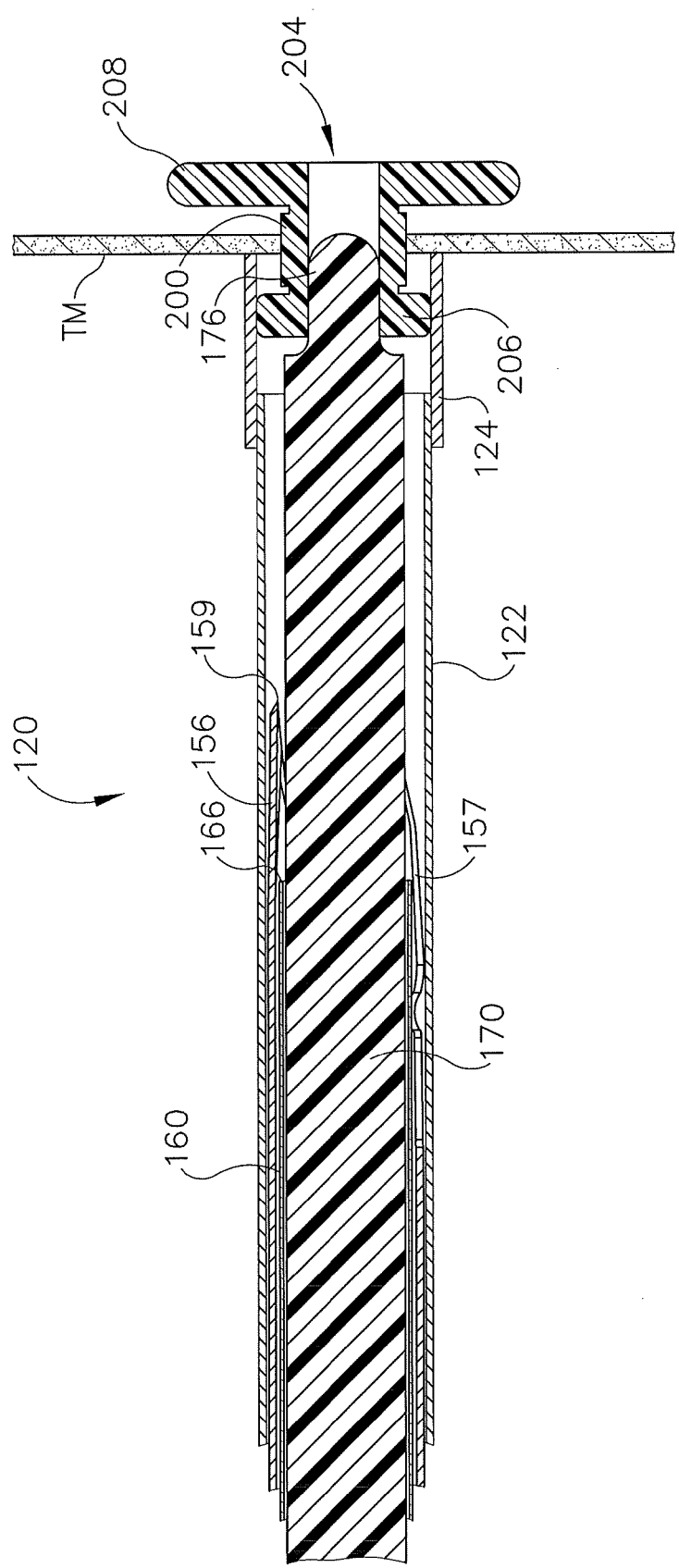
FIG. 22E depicts a cross-sectional side elevational view of the distal end of the shaft assembly of FIG. 4A engaged with a tympanic membrane, with the shield tube of FIG. 22C retracted proximally, with the PE tube of FIG. 20 in a partially expanded state.
Figure 22F:
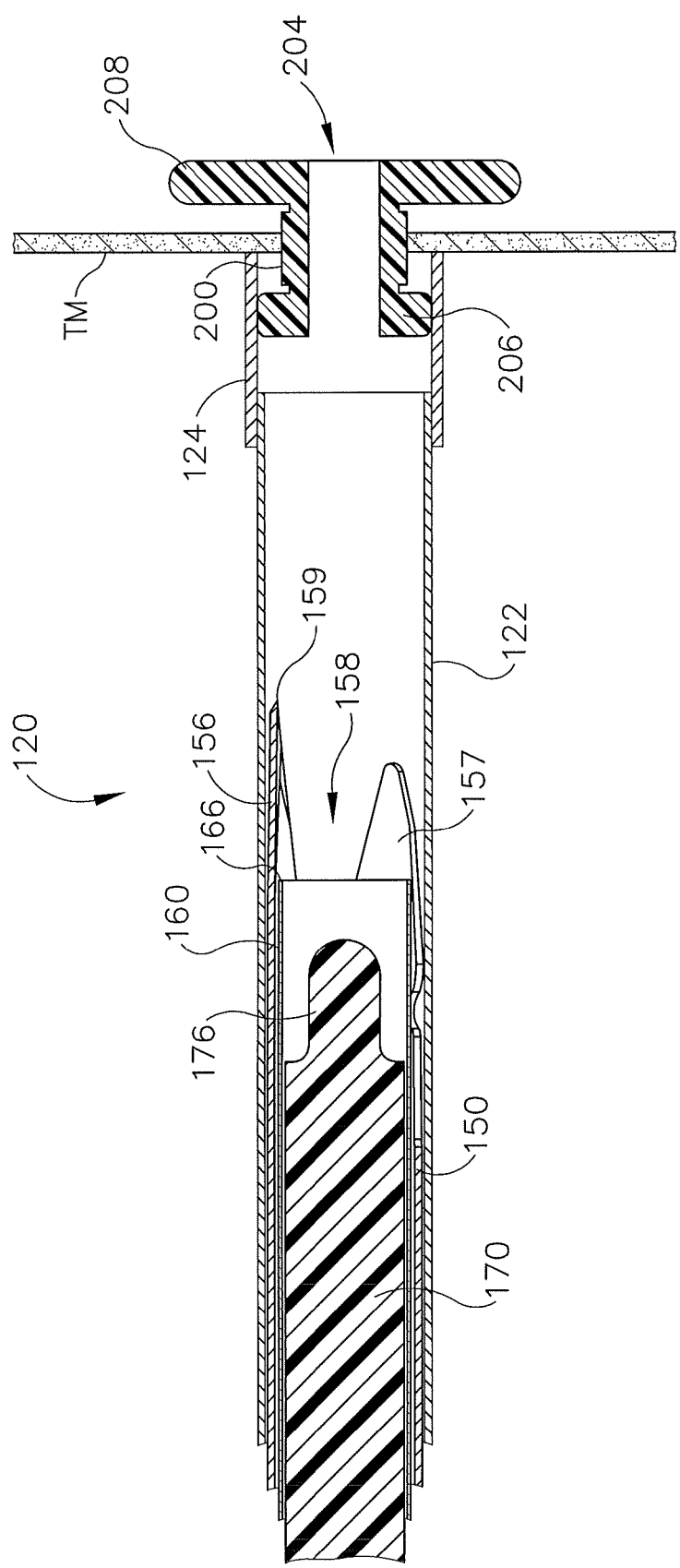
FIG. 22F depicts a cross-sectional side elevational view of the distal end of the shaft assembly of FIG. 4A engaged with a tympanic membrane, with the plunger of FIG. 22C retracted proximally so as to leave the PE tube of FIG. 20 within the tympanic membrane, with the PE tube of FIG. 20 in a partially expanded state.

Once camshaft (130) starts rotating at the urging of torsion spring (140) upon actuation of trigger mechanism (106), pins (154, 164, 174) begin to ride along their respective tracks (132, 134, 136), such that piercer tip (159) and leaves (156, 157) are driven distally through the patient's tympanic membrane (TM) as shown in FIG. 22B. As camshaft (130) continues to rotate, tubes (160, 170) and PE tube (200) are advanced distally while piercer/dilator tube (150) remains longitudinally stationary. As shown in FIG. 22C, shield tube (160) spreads leaves (156, 157) outwardly from their default positions. This further dilates the puncture site in the tympanic membrane (TM). Shield tube (160) continues to contain PE tube (200) at this stage. As camshaft (130) continues to rotate, piercer/dilator tube (150) retracts proximally behind clear tip member (124) as shown in FIG. 22D while tubes (160, 170) remain longitudinally stationary. Shield tube (160) then begins to retract proximally, while pusher tube (170) remains longitudinally stationary, as shown in FIG. 22E. This relative movement uncovers the distal end of PE tube (200), such that the resilient bias of petals (208) causes petals (208) to flex to transverse positions, thereby effectively forming a flange on the far side of the tympanic membrane (TM). Piercer/dilator tube (150) eventually returns to the fully proximal position, and pusher tube (170) eventually reaches a fully distal position. As camshaft (130) continues to rotate, shield tube (160) continues to retract proximally. This relative movement uncovers the proximal end of PE tube (200), such that the resilient bias of PE tube (200) is allowed to form flange (206) on the near side of the tympanic membrane (TM). As camshaft (130) continues to rotate, pusher tube (170) is retracted proximally as shown in FIG. 22F.

Figure 22G:
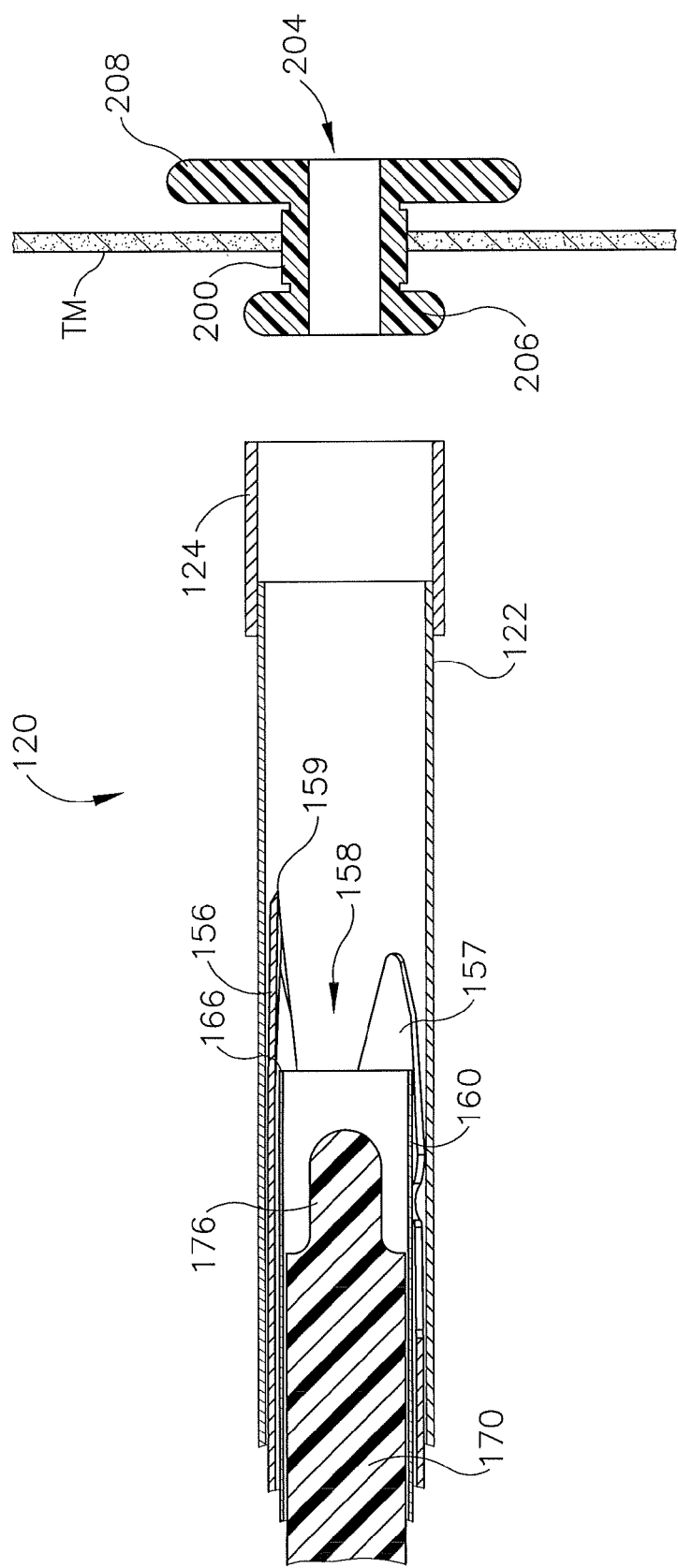
FIG. 22G depicts a cross-sectional side elevational view of the distal end of the shaft assembly of FIG. 4A retracted proximally from a tympanic membrane, with the PE tube of FIG. 20 in a completely expanded state.
Figure 23:
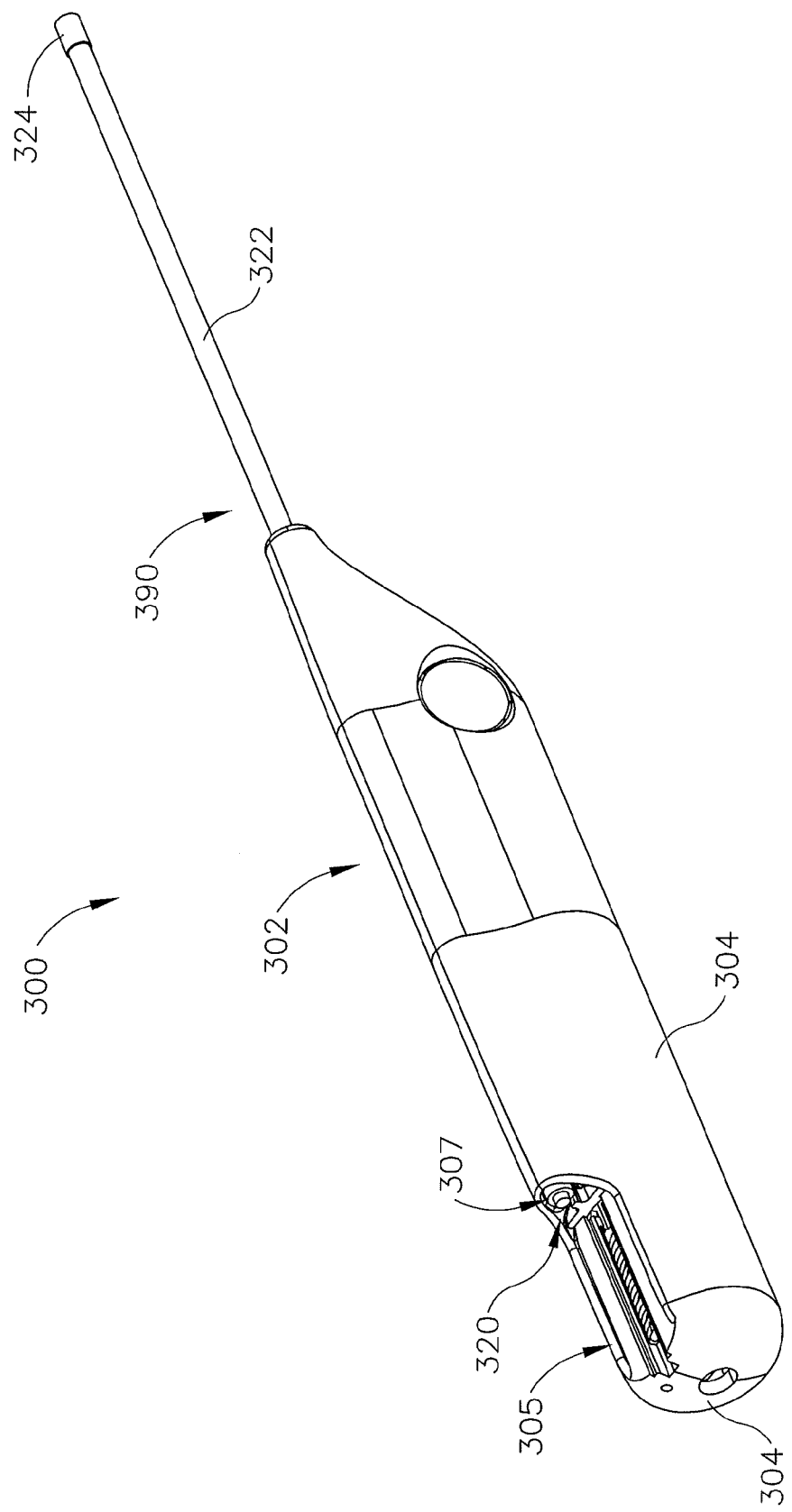
FIG. 23 depicts a perspective view of an exemplary alternative PETDD.
Figure 24:
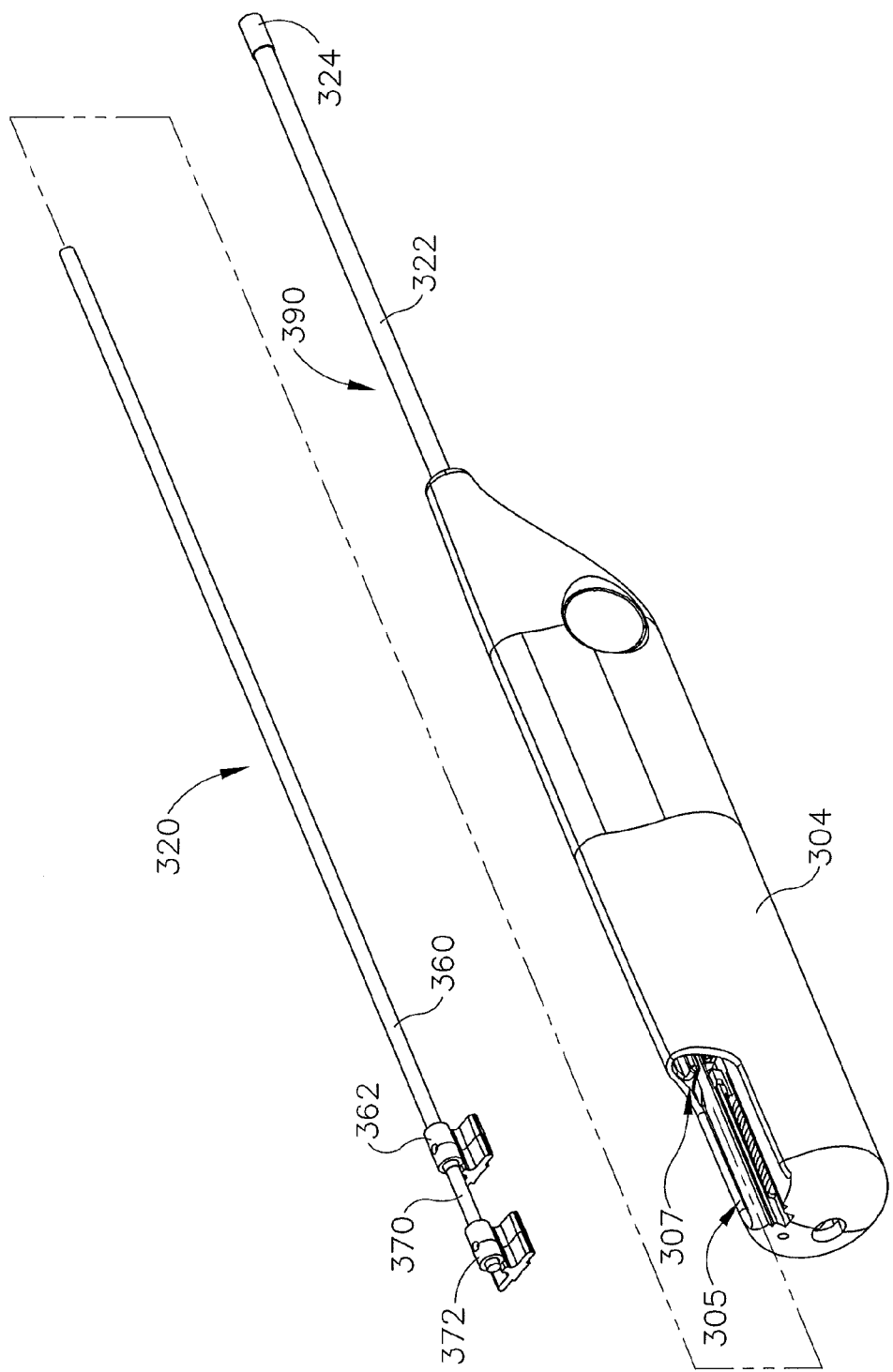
FIG. 24 depicts a partially exploded perspective view of the PETDD of FIG. 23.

Upon completion of the above described sequence shown in FIGS. 22A-22F, cannula (120) is withdrawn from the patient's ear, leaving the actuated PE tube (200) in place in the patient's tympanic membrane (TM) as shown in FIG. 22G. Petals (208) and flange (206) cooperate to maintain the position of PE tube (200) in TM, while the passageway (204) formed by the interior of PE tube (200) (see FIGS. 16-20) provides a path for fluid communication (e.g., venting) between the patient's middle ear and outer ear. This fluid path further provides pressure equalization between the patient's middle ear and outer ear and/or promotes drainage of fluid from the middle ear via the Eustachian tube.

If the operator desires to perform the procedure on the patient's other ear, the operator may remove the spent shaft assembly (120) from handpiece (102), re-cock torsion spring (140), reset trigger mechanism (106), and load a new shaft assembly (120) into handpiece (102). It should therefore be understood that only shaft assembly (120) needs to be replaced for each procedure. Torsion spring (140) may be re-cocked by rotating cam shaft (130) via a hexagonal socket formed in a proximal end of camshaft (130). In some instances, a separate tool may be provided with PETDD (100) to facilitate rotation of cam shaft (130) via the hexagonal socket. In some other versions, a knob or other feature may be provided on handpiece (102) (or may otherwise be integrated with handpiece (102)) to provide re-cocking of torsion spring (140). If the operator desires to perform the procedure on another patient, the operator may sterilize and reuse handpiece (102), such that for different patients, only shaft assembly (120) needs to be replaced for each procedure.

It should be understood that the foregoing components, features, and operabilities of PETDD (100) are merely illustrative examples. A PETDD (100) may include various other features in addition to or in lieu of those described above. By way of example only, any of the devices herein may also include one or more of the various features disclosed in any of the various references that are incorporated by reference herein. By way of further example only, some variations of PETDD (100) may lack a PE tube (200). Some such versions of PETDD (100) may also lack a shield tube (160) and a pusher tube (170). For instance, some such versions of PETDD (100) may just include a piercing element that is configured to pierce a tympanic membrane (TM), simply to provide an opening for fluid drainage or otherwise. Such a piercing element may be configured similar to piercer/dilator tube (150). Alternatively, such a piercing element may have a closed sharp tip. For instance, such a closed sharp tip may be configured in accordance with the teachings of any of the references cited herein. Other suitable forms that a piercing element may take will be apparent to those of ordinary skill in the art in view of the teachings herein. Some additional merely illustrative variations of PETDD (100) will be described in greater detail below, while other variations of PETDD (100) will be apparent to those of ordinary skill in the art in view of the teachings herein.

II. Exemplary Alternative Pressure Equalization Tube Delivery Instrument

FIGS. 23-29B show an exemplary alternative PETDD (300). PETDD (300) and its components are configured to operate substantially similarly to PETDD (100) discussed above except for the differences discussed below. PETDD (300) of this example comprises a handpiece (302), a proximal shaft assembly (320), and a distal shaft assembly (390) extending distally from handpiece (302). As will be discussed in more detail below, proximal shaft assembly (320) is coaxially and slidably disposed within distal shaft assembly (390). Hanpdiece (302) is formed by two housing (304) halves that are joined together and that include internal features configured to support various components of PETDD (300). Handpiece (302) is configured to be handheld, such that an operator may fully operate PETDD (300) using a single hand. Distal shaft assembly (390) of the present example comprises an elongate cannula (322) having a clear tip member (324) at the distal end of cannula (322). Clear tip member (324) is configured to contact a patient's tympanic membrane (TM) while enabling visualization of the distal end of cannula (322). In some versions, tip member (324) is formed of a soft or elastomeric material such as rubber, soft plastic, etc. This may dampen vibrations that might otherwise be transmitted from cannula (322) to the patient's tympanic membrane (TM) during firing of PETDD (300). In addition or in the alternative, tip member (324) may include some other kind of dampening feature as will be apparent to those of ordinary skill in the art in view of the teachings herein.

Figure 25:
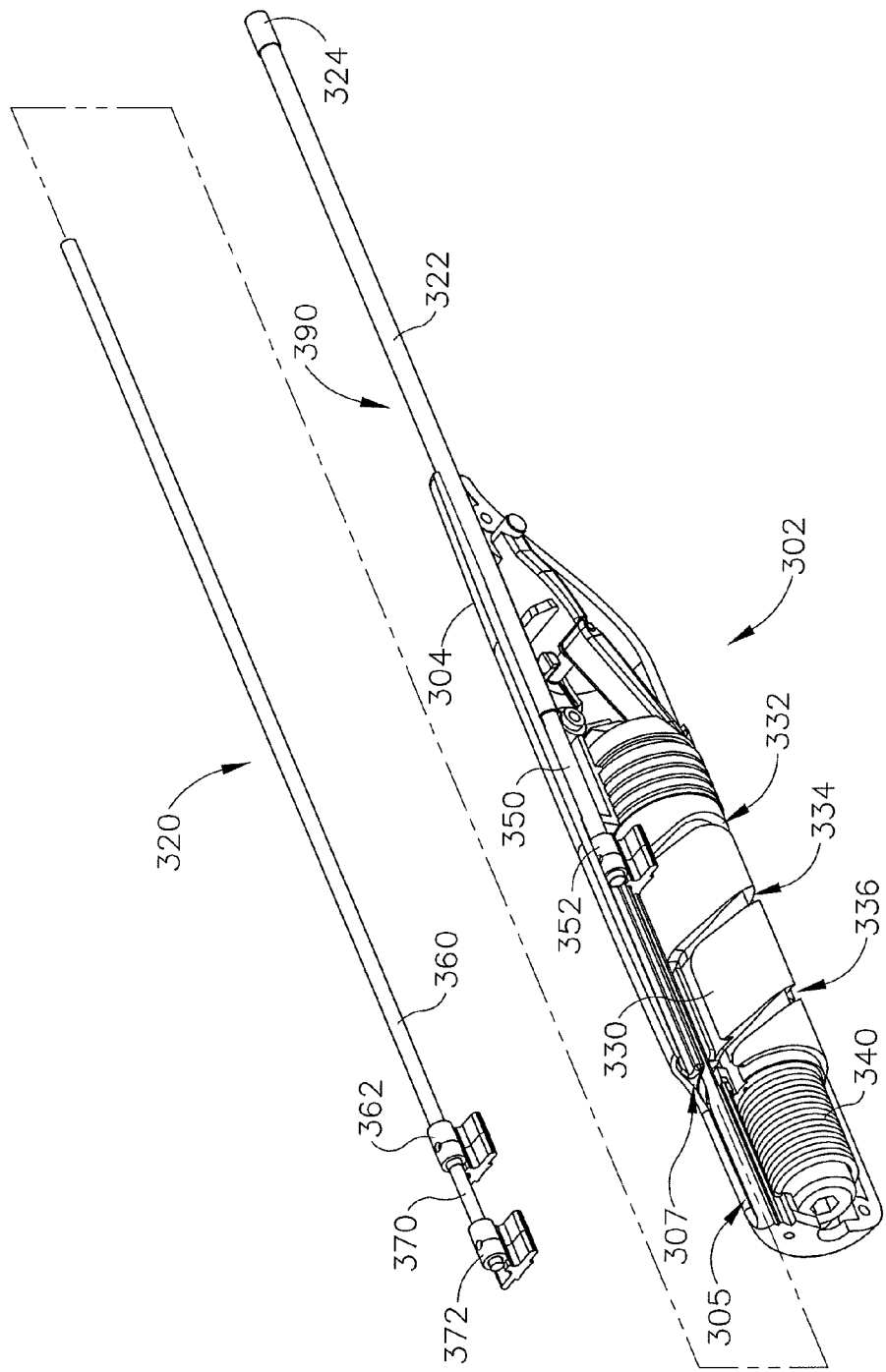
FIG. 25 depicts a partially exploded perspective view of the PETDD of FIG. 23, with a housing half omitted.

As can be seen in FIG. 25, housing (304) supports a camshaft (330) and various other components. Camshaft (330) includes a piercer/dilator track (332), a shield tube track (334), and a pusher track (336). Tracks (332, 334, 336) are formed as recesses in camshaft (330) and each track (332, 334, 336) has a unique configuration in order to provide a particular sequence of operation of translating components. A torsion spring (340) is coupled to the proximal end of camshaft (330). Torsion spring (340) is also grounded against housing (304). Torsion spring (340) resiliently provides a rotational bias to camshaft (330). In particular, torsion spring (340) urges camshaft (330) to rotate in the clockwise direction (viewed from the distal end of PETDD (300) toward the proximal end of PETDD (300)) about the longitudinal axis of camshaft (330). A trigger mechanism (306) selectively resists such rotation. By way of example only, trigger mechanism (306) may be configured to operate in accordance with at least some of the teachings of U.S. patent application Ser. No. 13/804,553, entitled "Features to Improve and Sense Tympanic Membrane Apposition by Tympanostomy Tube Delivery Instrument," filed Mar. 14, 2013; and/or U.S. patent application Ser. No. 14/457,412, entitled "Trigger Assembly for Tympanostomy Tube Delivery Device," filed Aug. 12, 2014, the disclosures of which are incorporated by reference herein. While torsion spring (340) is used to bias camshaft (330) in the present example, it should be understood that any other suitable types of components may be used to bias camshaft (330).

As best seen in FIG. 2, housing halves (304) of handpiece (302) define a proximal elongate channel (305). Channel (305) extends longitudinally along a proximal portion of handpiece (302). Housing halves (304) further define a proximal opening (307) which provides access to an interior of handpiece (302) via channel (305). Opening (307) is coaxially aligned with distal shaft assembly (390). As mentioned above, proximal shaft assembly (320) is coaxially and slidably disposed within distal shaft assembly (390). Distal shaft assembly (390) comprises a piercer/dilator tube (350) and cannula (322). Cannula (322) and piercer/dilator tube (350) are configured to operate substantially similar to cannula (122) and piercer/dilator tube (150), respectively, as discussed above, except for the differences discussed below. Piercer/dilator tube (350) is coaxially disposed within cannula (322). Piercer/dilator tube (350) is configured to translate relative to cannula (322). Proximal shaft assembly (320) comprises a shield tube (360) and a pusher tube (370). Shield tube (360) and pusher tube (370) are configured to operate substantially similar to shield tube (160) and pusher tube (170), respectively, as discussed above, except for the differences discussed below. Pusher tube (370) is coaxially and slidably disposed within shield tube (360). Thus, with proximal shaft assembly (320) disposed within distal shaft assembly (390), pusher tube (370) is coaxially and slidably disposed within shield tube (360), which is coaxially and slidably disposed within piercer/dilator tube (350), which is coaxially and slidably disposed within cannula (322). Tubes (350, 360, 370) all translate relative to cannula (322) in a particular sequence in order to deploy a PE tube (200) as described above with reference to PETDD (100). This sequence is driven by rotation of camshaft (330).

A cam follower (352) is fixedly secured to the proximal end of piercer/dilator tube (350). Cam follower (352) includes a laterally projecting pin (354) that is disposed within piercer/dilator track (332), such that rotation of camshaft (330) causes cam follower (352) and piercer/dilator tube (350) to translate. Similarly, a cam follower (362) is fixedly secured to the proximal end of shield tube (360). Cam follower (362) includes a laterally projecting pin (364) that may be disposed within shield tube track (334), such that rotation of camshaft (330) causes cam follower (362) and shield tube (360) to translate. A cam follower (372) is fixedly secured to the proximal end of pusher tube (370). Cam follower (372) includes a laterally projecting pin (374) that may be disposed within pusher tube track (336), such that rotation of camshaft (330) causes cam follower (372) and pusher tube (370) to translate.

Figure 26:
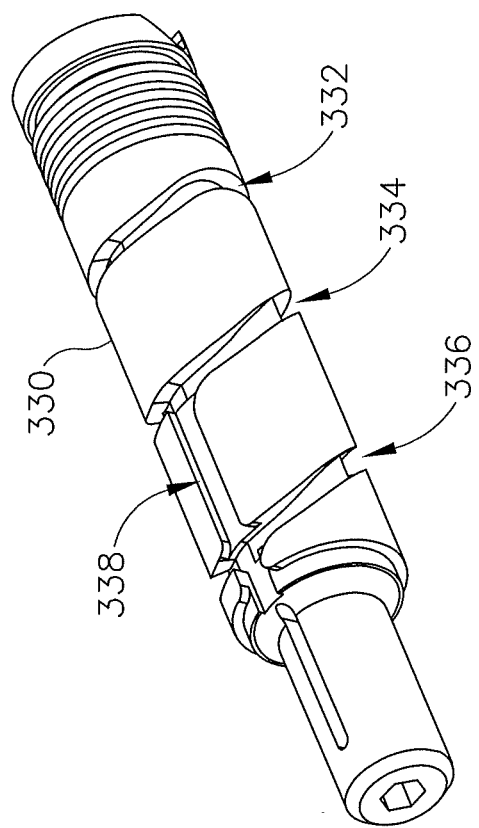
FIG. 26 depicts a perspective view of a camshaft of the PETDD of FIG. 23.
Figure 27:
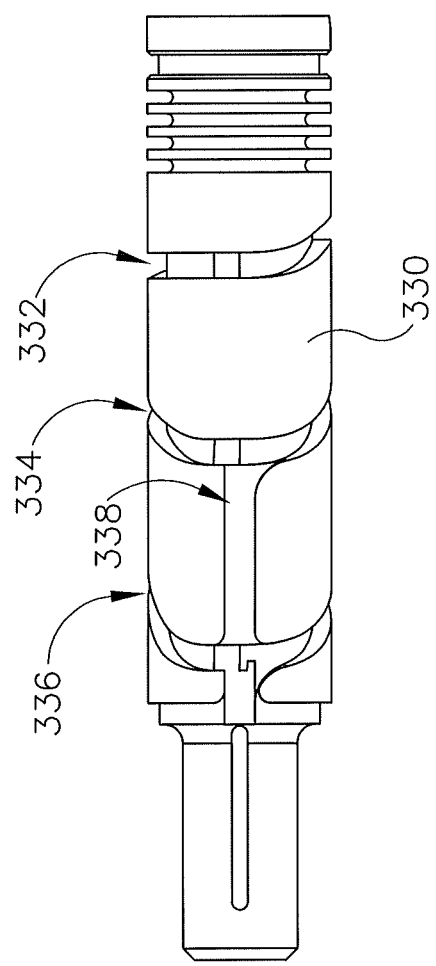
FIG. 27 depicts a top view of the camshaft of FIG. 26.
Figure 28:
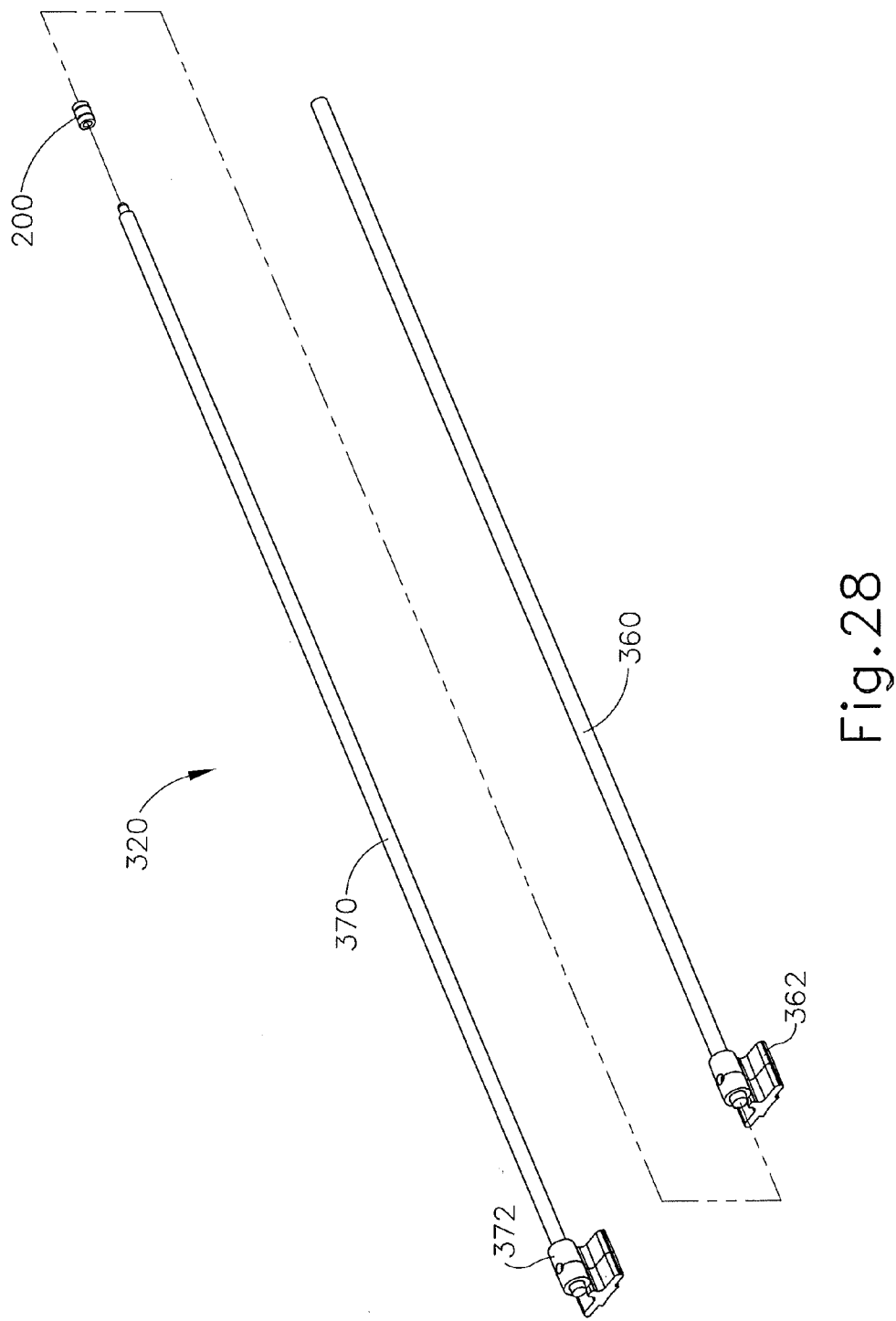
FIG. 28 depicts an exploded perspective view of a shaft assembly of the PETDD of FIG. 23.

As best seen in FIG. 25, housing (304) supports distal shaft assembly (390). In particular, cannula (322) of distal shaft assembly (390) is fixedly coupled with housing (304) such that distal shaft assembly (390) is not removable from handpiece (302) without disassembling housing (304). Piercer/dilator tube (350) extends proximally from cannula (322) such that pin (354) of follower (352) is disposed within piercer/dilator track (332). Piercer/dilator tube (350) includes a proximal opening such that proximal shaft assembly (320) may be received within piercer/dilator tube (350) of distal shaft assembly (390). Thus, it should be understood that in contrast with distal shaft assembly (390), proximal shaft assembly (320) may be selectively coupled with handpiece (302). As shown in FIGS. 26 and 27, camshaft (330) includes an elongate, longitudinally extending channel (338) formed in a top surface of camshaft (330). Channel (338) is configured to receive pins (364, 374) of followers (362, 372) as proximal shaft assembly (320) is inserted into distal shaft assembly (390).

Figure 29A:
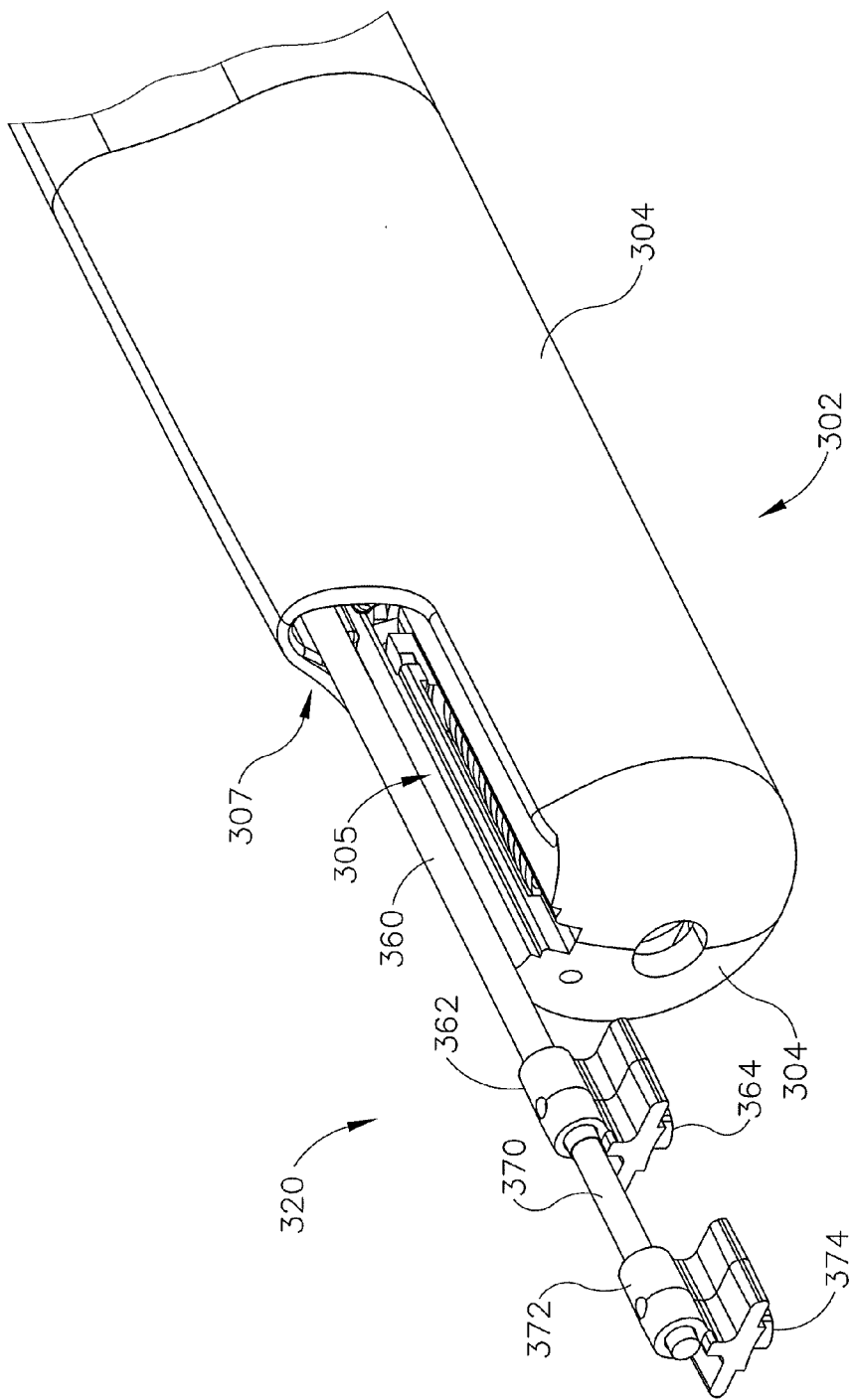
FIG. 29A depicts a perspective view of a proximal portion of the PETDD of FIG. 23 with the shaft assembly of FIG. 28 partially disposed within the PETDD.

As shown in FIGS. 29A and 29B, proximal shaft assembly (320) may be coupled with camshaft (330) via insertion of proximal shaft assembly (320) within distal shaft assembly (390) via channel (305) and distal opening (307). In other words, proximal shaft assembly (320) is coupled with handpiece (302) by moving proximal shaft assembly (320) along a path that is coaxial with a longitudinal axis of distal shaft assembly (390) and parallel to a longitudinal axis of handpiece (302). Upon insertion of proximal shaft assembly (320) within distal shaft assembly (390), pins (364, 374) of followers (362, 372) of proximal shaft assembly (320) pass within channel (338) of camshaft (330) and engage tracks (334, 336) respectively. Housing (304) may include a detent, latch, or other feature that prevents proximal shaft assembly (320) from sliding proximally out of handpiece (302) after proximal shaft assembly (320) has been inserted within handpiece (302). Therefore, it should be appreciated that rotation of camshaft (330) will actuate piercer/dilator tube (350), shield tube (360), and pusher tube (370) via followers (352, 362, 372). As mentioned above, tubes (350, 360, 370) all translate relative to cannula (322) in a particular sequence in order to deploy PE tube (200) as was described above with reference to PETDD (100). This sequence is driven by rotation of camshaft (330). It should be appreciated that proximal shaft assembly (320) may comprise features configured to maintain a distance between follower (362) and follower (372) during insertion of proximal shaft assembly (320) within distal shaft assembly (390). Such features may further be configured to allow translation of shield tube (360) and pusher tube (370) relative to one another via camshaft (330) rotation upon insertion of shaft proximal shaft assembly (320) into handpiece (302). It should further be appreciated that PE tube (200) may be preloaded within proximal shaft assembly (320) before proximal shaft assembly (320) is inserted with handpiece (302).

If the operator desires to reuse PETDD (300) to perform the procedure on the patient's other ear, the operator may remove the spent proximal shaft assembly (320) from handpiece (302), re-cock torsion spring (340), reset trigger mechanism (306), and load a new proximal shaft assembly (320) into handpiece (302). It should therefore be understood that only proximal shaft assembly (320) needs to be replaced for each procedure. Torsion spring (340) may be re-cocked by rotating cam shaft (330) via a hexagonal socket formed in a proximal end of camshaft (330). In some instances, a separate tool may be provided with PETDD (300) to facilitate rotation of cam shaft (330) via the hexagonal socket. In some other versions, a knob or other feature may be provided on handpiece (302) (or may otherwise be integrated with handpiece (102)) to provide re-cocking of torsion spring (340). If the operator desires to perform the procedure on another patient, the operator may sterilize and reuse the combination of handpiece (302) and distal shaft assembly (390), such that for different patients, only proximal shaft assembly (320) needs to be replaced for each procedure.

It should be understood that the foregoing components, features, and operabilities of PETDD (300) are merely illustrative examples. A PETDD (300) may include various other features in addition to or in lieu of those described above. By way of example only, any of the devices herein may also include one or more of the various features disclosed in any of the various references that are incorporated by reference herein. By way of further example only, some variations of PETDD (300) may lack a PE tube (200). Some such versions of PETDD (300) may also lack a shield tube (360) and a pusher tube (370). For instance, some such versions of PETDD (300) may just include a piercing element that is configured to pierce a tympanic membrane (TM), simply to provide an opening for fluid drainage or otherwise. Such a piercing element may be configured similar to piercer/dilator tube (350). Alternatively, such a piercing element may have a closed sharp tip. For instance, such a closed sharp tip may be configured in accordance with the teachings of any of the references cited herein. Other suitable forms that a piercing element may take will be apparent to those of ordinary skill in the art in view of the teachings herein. Similarly, other variations of PETDD (300) will be apparent to those of ordinary skill in the art in view of the teachings herein.

III. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In some instances, the device is sterilized using conventional ethylene oxide sterilization techniques and systems. In some other instances, the device is placed in a closed and sealed container, such as a plastic or TYVEK bag; and the container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, steam, etc.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An instrument, comprising:
   (a) a shaft assembly including a plurality of coaxially-arranged shafts and a tympanostomy tube, wherein at least two shafts of the plurality of coaxially-arranged shafts include respective cam followers;
   (b) a handpiece body, the handpiece body defining an opening in an external surface of the handpiece body, the handpiece body configured to removably receive the at least two shafts of the plurality of coaxially-arranged shafts and the respective cam followers through the opening such that the shaft assembly extends distally from the handpiece body, the opening including an elongate channel and a plurality of slots such that the plurality of slots intersect the elongate channel, the plurality of slots configured to receive the cam followers; and
   (c) a drive assembly disposed within the handpiece body, the drive assembly including a cam configured to engage the cam followers upon insertion of the at least two shafts of the plurality of coaxially-arranged shafts through the opening, wherein the drive assembly is operable to drive the plurality of coaxially-arranged shafts of the shaft assembly in a predetermined sequence to deploy the tympanostomy tube.

2. The instrument of claim 1, wherein the entire shaft assembly is selectively removable and coupleable with the handpiece body.

3. The instrument of claim 1, wherein only a portion of the shaft assembly is selectively removable and coupleable with the handpiece body.

4. The instrument of claim 1, wherein the elongate channel is configured to be coupled with the shaft assembly in a snap-fit manner.

5. The instrument of claim 1, wherein the cam followers are configured to slide within the elongate channel.

6. The instrument of claim 1, wherein the opening includes a distal opening.

7. The instrument of claim 1, wherein the at least two shafts of the plurality of coaxially-arranged shafts include a piercer/dilator tube, a shield tube, a pusher tube, and a cannula.

8. The instrument of claim 7, wherein the piercer/dilator tube, the shield tube, the pusher tube, and the cannula are selectively removable and coupleable with the handpiece body.

9. The instrument of claim 7, wherein the shield tube and the pusher tube are selectively removable and coupleable with the handpiece body.

10. The instrument of claim 7, wherein the cannula is coupled to the handpiece body.

11. The instrument of claim 7, wherein the pusher tube is disposed within the shield tube, the shield tube is disposed within the piercer/dilator tube, and the piercer/dilator tube is disposed within the cannula.

12. The instrument of claim 1, wherein the at least two shafts of the plurality of coaxially-arranged shafts include a piercer/dilator tube, the piercer/dilator tube including a plurality of resilient leaves.

13. The instrument of claim 12, wherein at least one of the resilient leaves includes a sharp distal tip configured to pierce a tympanic membrane.

14. The instrument of claim 1, wherein the shaft assembly comprises features configured to maintain a distance between the at least two shafts of the plurality of coaxially-arranged shafts upon insertion of the at least two shafts of the plurality of coaxially-arranged shafts in the opening.

15. The instrument of claim 1, wherein the handpiece body includes a first housing portion and a second housing portion, the first housing portion and the second housing portion configured to be coupled together to form the handpiece body, the first housing portion and the second housing portion, when coupled together, collectively defining the opening.

16. An instrument, comprising:
   (a) a shaft assembly including a plurality of coaxially arranged shafts, wherein at least one shaft of the plurality of coaxially arranged shafts includes a distal end having a piercing element, wherein the at least one shaft including the piercing element further includes a cam follower;
   (b) a handpiece body, the handpiece body defining a laterally-presented channel in an external surface of the handpiece body, the handpiece body configured to removably receive the at least one shaft and the cam follower through the laterally-presented channel such that the shaft assembly extends distally from the handpiece body, the laterally-presented channel including a plurality of slots such that the plurality of slots intersect the laterally-presented channel, at least one of the plurality of slots configured to receive the cam follower; and
   (c) a drive assembly disposed within the handpiece body, the drive assembly including a cam configured to engage the cam follower upon insertion of the at least one shaft in the laterally-presented channel, wherein the drive assembly is operable to drive the at least one shaft including the piercing element.

17. The instrument of claim 16, wherein the handpiece body includes a first housing portion and a second housing portion, the first housing portion and the second housing portion configured to be coupled together to form the handpiece body, the first housing portion and the second housing portion, when coupled together, collectively defining the laterally-presented channel.

18. A method of using an instrument, the instrument comprising a handpiece body, a shaft assembly extending distally from the handpiece body, the shaft assembly including a plurality of coaxially-arranged shafts and a tympanostomy tube, at least two shafts of the plurality of coaxially-arranged shafts including respective cam followers, and a drive assembly disposed within the handpiece body, the drive assembly including a cam, the method comprising the steps of:
   inserting the at least two shafts of the plurality of coaxially-arranged shafts and the respective cam followers through an opening defined in an external surface of the handpiece body, the opening including an elongate channel and a plurality of slots such that the plurality of slots intersect the elongate channel, the plurality of slots configured to receive the cam followers, wherein the step of inserting the at least two shafts causes the cam of the drive assembly to engage the cam followers of the shaft assembly; and actuating the drive assembly to thereby drive the at least two shafts of the plurality of coaxially-arranged shafts in a predetermined sequence to deploy the tympanostomy tube.

19. The method of claim 18, wherein the at least two shafts of the plurality of coaxially-arranged shafts includes at least one of a piercer/dilator tube, a shield tube, a pusher tube, and a cannula.

20. The method of claim 19, further comprising the step of removing the at least two shafts from the handpiece body after completion of a procedure.

* * * * *